United States Patent [19]

Kawamura et al.

[11] Patent Number: 5,426,188
[45] Date of Patent: Jun. 20, 1995

[54] IMINOTHIAZOLINES, THEIR PRODUCTION AND USE AS HERBICIDES, AND INTERMEDIATES FOR THEIR PRODUCTION

[75] Inventors: Shinichi Kawamura, Osaka; Keiichi Izumi, Minoo; Junichi Sato, Toyonaka; Yuzuru Sanemitsu, Ashiya, all of Japan; Tatsuhiro Hamada, Bourgogne, France; Hideyuki Shibata, Toyonaka, Japan; Ryo Sato, Dyrham, N.C.

[73] Assignee: Sumitomo Chemical Company, Limited, Osaka, Japan

[21] Appl. No.: 5,050

[22] Filed: Jan. 15, 1993

Related U.S. Application Data

[60] Division of Ser. No. 769,485, Oct. 1, 1991, Pat. No. 5,244,863, which is a continuation-in-part of Ser. No. 668,986, Mar. 12, 1991, abandoned.

[30] Foreign Application Priority Data

| | | |
|---|---|---|
| Mar. 12, 1990 [JP] | Japan | 2-62172 |
| Jul. 13, 1990 [JP] | Japan | 2-185933 |
| Nov. 28, 1990 [JP] | Japan | 2-331071 |
| Sep. 11, 1991 [JP] | Japan | 3-231851 |

[51] Int. Cl.[6] .............. C07D 277/46; C07D 277/48; C07D 277/40
[52] U.S. Cl. .................. 548/193; 548/195; 548/196; 548/199
[58] Field of Search .............. 548/195, 196, 199, 193

[56] References Cited

U.S. PATENT DOCUMENTS

| | | | |
|---|---|---|---|
| 4,103,017 | 7/1978 | Davies et al. | 548/193 |
| 4,913,722 | 4/1990 | Felix et al. | 548/193 |

FOREIGN PATENT DOCUMENTS

| | | |
|---|---|---|
| 300906 | 1/1989 | European Pat. Off. . |
| 318253 | 5/1989 | European Pat. Off. . |
| 349282 | 3/1990 | European Pat. Off. . |
| 349283 | 3/1990 | European Pat. Off. . |
| 384244 | 8/1990 | European Pat. Off. . |
| 432600 | 6/1991 | European Pat. Off. . |
| 2343735 | 7/1977 | France . |
| 941288 | 4/1956 | Germany . |

*Primary Examiner*—Robert Gerstl
*Attorney, Agent, or Firm*—Birch, Stewart, Kolasch & Birch

[57] ABSTRACT

An iminothiazoline compound of the formula:

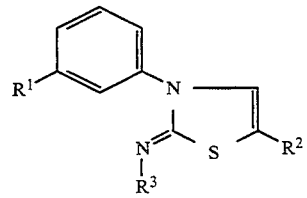

which is useful as a herbicide.

9 Claims, No Drawings

IMINOTHIAZOLINES, THEIR PRODUCTION AND USE AS HERBICIDES, AND INTERMEDIATES FOR THEIR PRODUCTION

This application is a divisional of application Ser. No. 07/769,485, filed on Oct. 1, 1991, now U.S. Pat. No. 5,344,863, which is a continuation-in-part of application Ser. No. 07/668,986 filed on Mar. 12, 1991 abandoned, the entire contents of which are hereby incorporated by reference.

This is a continuation-in-part application of our co-pending application Ser. No. 07/66.8,986 filed on Mar. 12, 1991 .

The present invention relates to iminothiazolines, their production and use as herbicides, and intermediates for their production. More particularly, it relates to iminothiazoline compounds having strong herbicidal potency and showing noticeable selectivity between crop plants and weeds, and intermediate compounds for production of said iminothiazoline compounds.

Some certain iminothiazolidine derivatives are known to be useful as active ingredients in herbicidal compositions (cf. EP-A-0349282). However, their herbicidal potency is not sufficiently high, or their selectivity between crop plants and weeds is not always sufficient. Thus, they can hardly be said to be satisfactory herbicides.

An extensive study has been made seeking satisfactory herbicides, and as the result, it has been found that iminothiazoline compounds of the formula:

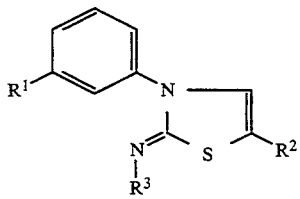

(I)

wherein $R^1$ is a halogen atom, a halogen-substituted $C_1$-$C_2$ alkyl group or a halogen-substituted $C_1$-$C_2$ alkyloxy group, $R^2$ is a methyl group, an ethyl group, a chlorine atom, a bromine atom or an iodine atom and $R^3$ is a formyl group, a $C_1$-$C_6$ alkylcarbonyl group, a benzylcarbonyl group, a $C_3$-$C_4$ alkenyloxycarbonyl group, a $C_3$-$C_4$ alkynyloxycarbonyl group, a $C_1$-$C_6$ alkyloxycarbonyl group, a $C_1$-$C_6$ alkyloxycarbonyl group substitued with $C_1$-$C_2$ alkyloxy or phenyl, a cyclo-($C_3$-$C_6$) alkylcarbonyl group, a cyclo($C_3$-$C_6$) alkylcarbonyl group substituted with methyl, a cyclo($C_3$-$C_6$) alkyloxycarbonyl group, a benzoyl group, an N-($C_1$-$C_3$) alkylcarbamoyl group, a phenoxycarbonyl group, a halogen-substituted $C_1$-$C_6$ alkylcarbonyl group or a halogen-substituted $C_1$-$C_3$ alkylsulfonyl group, provided that when $R^2$ is a chlorine atom, a bromine atom or an iodine atom, $R^1$ is a halogen atom or a halogen-substituted $C_1$-$C_2$ alkyl group and $R^3$ is a $C_1$-$C_6$ alkylcarbonyl group, a $C_1$-$C_6$ alkyloxycarbonyl group, a $C_1$-$C_6$ alkyloxycarbonyl group substituted with $C_1$-$C_2$ alkyloxy or phenyl, a benzoyl group, a phenoxycarbonyl group or a halogen-substituted $C_1$-$C_6$ alkylcarbonyl group exhibit strong herbicidal potency, and some of them show noticeable selectivity between crop plants and weeds. This invention is based on the above finding.

In the foregoing and subsequent descriptions, the carbon number indicates that of a group (i.e. alkyl, alkenyl or alkynyl) immediately following the same. In case of a $C_1$-$C_6$ alkylcarbonyl group, for instance, the carbon number indicates that of its alkyl portion and does not include that of its carbonyl portion. In case of a $C_3$-$C_4$ alkynyloxycarbonyl group, the carbon number indicates that of its alkynyl portion and does not include that of its carbonyl portion.

Also, a group substituted with a substituent(s) (e.g. $C_1$-$C_2$ alkyloxy, phenyl, methyl) covers a group bearing 1 or 2 substituents. For instance, a $C_1$-$C_6$ alkyloxycarbonyl group substituted with $C_1$-$C_2$ alkyloxy or phenyl- covers a $C_1$-$C_6$ alkyloxycarbonyl group substituted with one or two $C_1$-$C_2$ alkyloxys and a $C_1$-$C_6$ alkyloxycarbonyl group substituted with 1 or 2 phenyls. The term "halogen-substituted" is intended to mean usually "substituted with not more than five halogens" particularly "substituted with not more than three halogens".

The iminothiazoline compounds (I) produce generally strong herbicidal activity against a wide variety of weeds including broad-leaved weeds and Graminaceous weeds in agricultural plowed fields by foliar or soil treatment without producing any material phytotoxicity to crop plants. Examples of the broad-leaved weeds include common purslane (*Portulaca oleracea*), common chickweed (*Stellaria media*), common lambsquarters (*Chenopodium album*), redroot pigweed (*Amaranthus retroflexus*), radish (*Raphanus sativus*), wild mustard (*Sinapis arvensis*), shepherdspurse (*Capsella bursa-pastoris*), hemp sesbania (*Sesbania exaltata*), sicklepod (*Cassia obtusifolia*), velvetleaf (*Abutilon theophrasti*), prickly sida (*Sida spinosa*), field pansy (*Viola arvensis*), catchweed bedstraw (*Galium aparine*), ivyleaf morningglory (*Ipomoea hederacea*), tall morningglory (*Ipomoea purpurea*), field bindweed (*Convolvulus arvensis*), purple deadnettle (*Lamium purpureum*), henbit (*Lamium amplexicaure*), jimsonweed (*Datura stramonium*), black nightshade (*Solanum nigrum*), persian speedwell (*Veronica persica*), common cocklebur (*Xanthium pensylvanicum*), common sunflower (*Helianthus annuus*), scentless chamomile (*Matricaria perforata*), corn marigold (*Chrysanthemum segetum*), etc. Examples of Graminaceous weeds include Japanese millet (*Echinochloa frumentacea*), barnyardgrass (*Echinochloa crus-galli*), green foxtail (*Setaria viridis*), yellow foxtail (*Setaria glauca*), southern crabgrass (*Digitaria ciliaris*), large crabgrass (*Digitaria sanquinalis*), annual bluegrass (*Poa annua*), blackgrass (*Alopecurus myosuroides*), oats (*Avena sativa*), wild oats (*Avena fatua*), johnsongrass (*Sorghum halepense*), quackgrass (*Agropyron repens*), downy brome (*Bromus tectorum*), giant foxtail (*Setaria faberi*), fall panicum (*Panicum dichotomiflorum*), shattercane (*Sorghum bicolor*), bermudagrass (*Cynodon dactylon*), etc. Advantageously, the iminothiazoline compounds (I) do not show any material chemical injury to various agricultural crops such as corn, wheat, barley, rice plant, soybean, cotton, sugar beet, etc., particularly to cotton.

The iminothiazoline compounds (I) are also effective in exterminating paddy field Weeds including Graminaceous weeds such as barnyardgrass (*Echinochloa oryzicola*), broad-leaved weeds such as common falsepimpernel (*Lindernia procumbens*), indian toothcup (*Rotala indica*), waterwort (*Elatine triandra*) and *Ammannia multiflora,* Cyperaceous weeds such as umbrella sedge (*Cyperus difformis*), hardstem bulrush (*Scirpus juncoides*), needle spikerush (*Eleocharis acicularis*) and water nutgrass (*Cyperus serotinus*), and others such as monochoria (*Monochoria vaginalis*) and arrowhead (*Sagittaria pygmaea*) without producing any phytotoxicity to rice plants on flooding treatment.

Among the iminothiazoline compounds (I), preferred are those wherein $R^1$ is a trifluoromethyl group; those wherein $R^2$ is a methyl group or an ethyl group; and those wherein $R^3$ is a $C_1-C_6$ alkylcarbonyl group, a $C_1-C_6$ alkyloxycarbonyl group, a $C_1-C_6$ alkyloxycarbonyl group substituted with $C_1-C_2$ alkyloxy or phenyl, a cyclo($C_3-C_6$)alkylcarbonyl group, a cyclo($C_3-C_6$) alkylcarbonyl group substituted with methyl, a cyclo($C_3-C_6$) alkyloxycarbonyl group, a benzoyl group or a halogen-substituted $C_1-C_6$ alkylcarbonyl group. With respect to $R^3$, more preferred are a $C_1-C_4$ alkylcarbonyl group, a $C_1-C_4$ alkyloxycarbonyl group, a $C_1-C_4$ alkyloxycarbonyl group substituted with $C_1-C_2$ alkyloxy or phenyl, a cyclo($C_3-C_6$) alkylcarbonyl group, a cyclo($C_3-C_6$) alkylcarbonyl group substituted with methyl, a cyclo($C_3-C_6$) alkyloxycarbonyl group, a benzoyl group and a halogen-substituted $C_1-C_4$ alkylcarbonyl group; furthermore preferred are a $C_1-C_4$ alkylcarbonyl group, a $C_1-C_4$ alkyloxycarbonyl group and a halogen-substituted $C_1-C_4$ alkylcarbonyl group; still more preferred is a halogen-subtituted $C_1-C_4$ alkylcarbonyl gorup; the most preferred are a difluoroacetyl group or a trifuluoroacetyl group. Typical examples of the most preferred compounds are as follows:

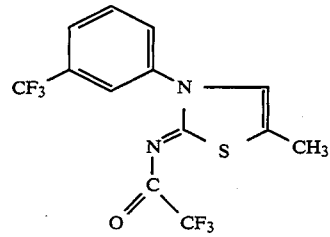

and

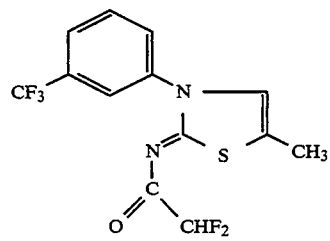

The iminothiazoline compounds (I) can be produced by various procedures, of which typical examples are shown in the following schemes I to III.

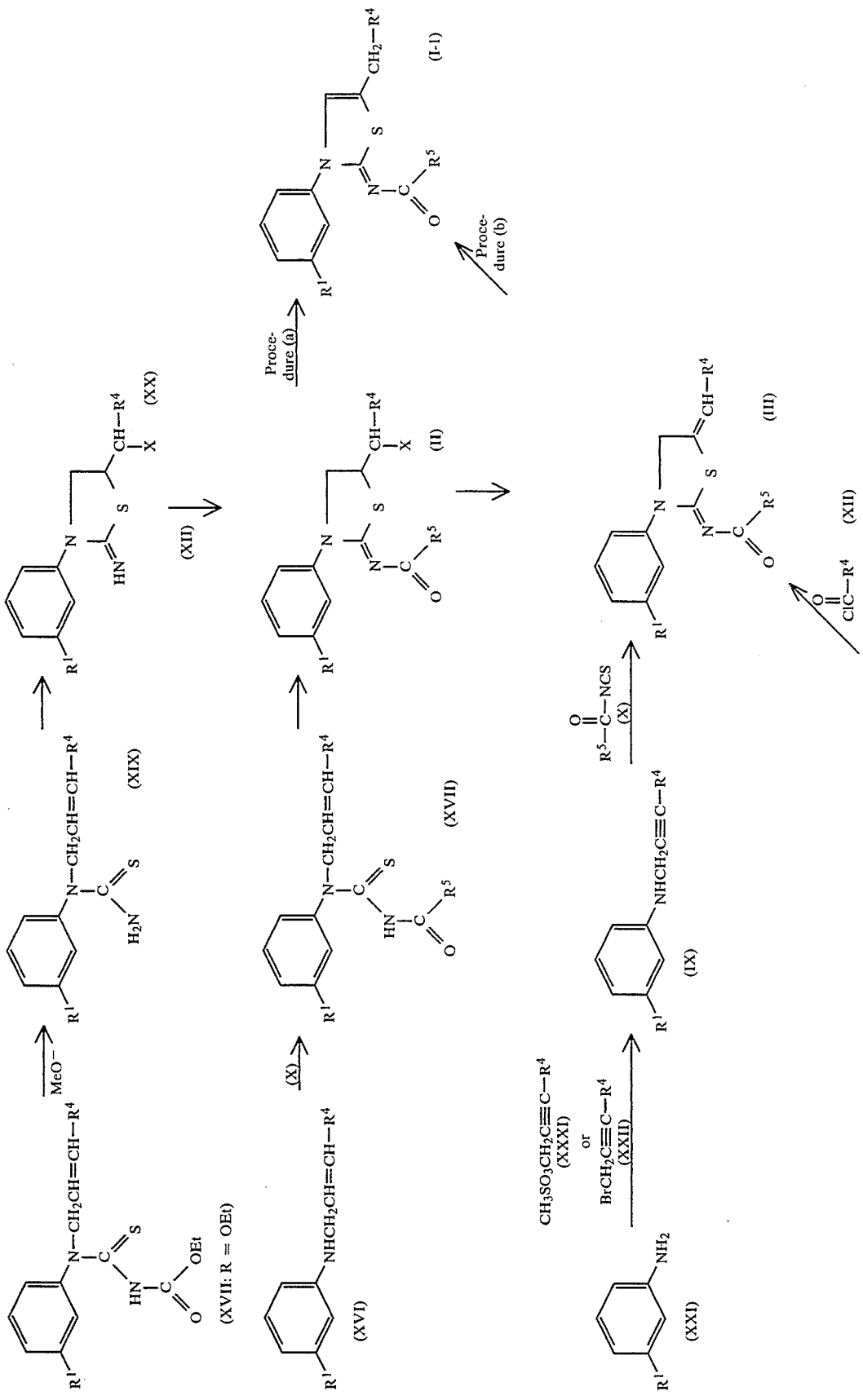

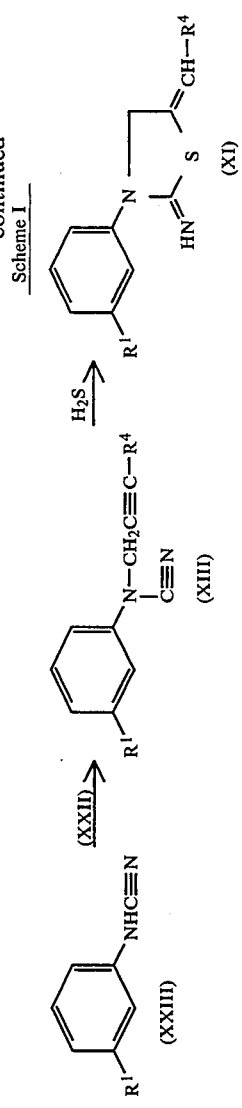

Scheme II
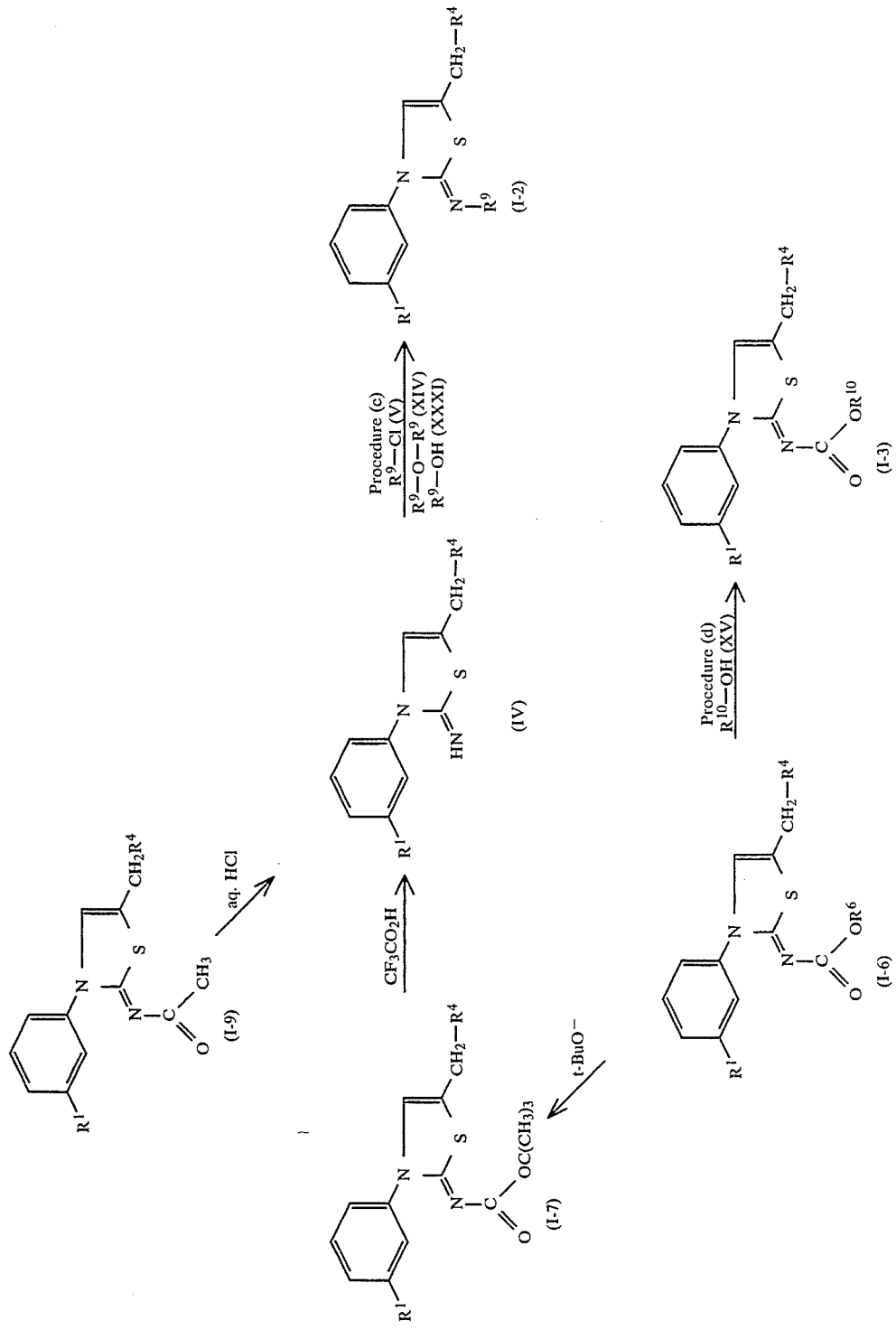

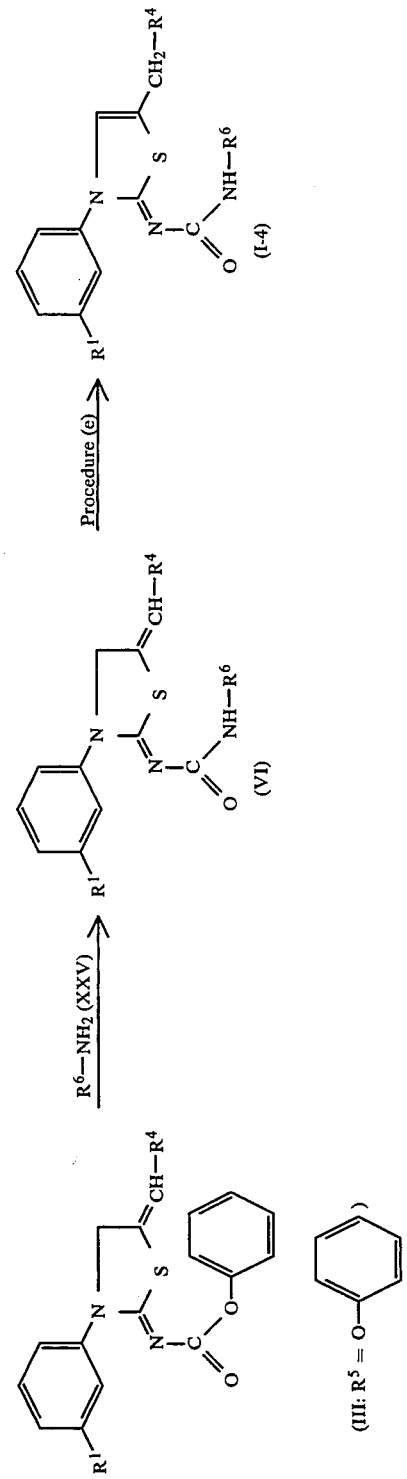

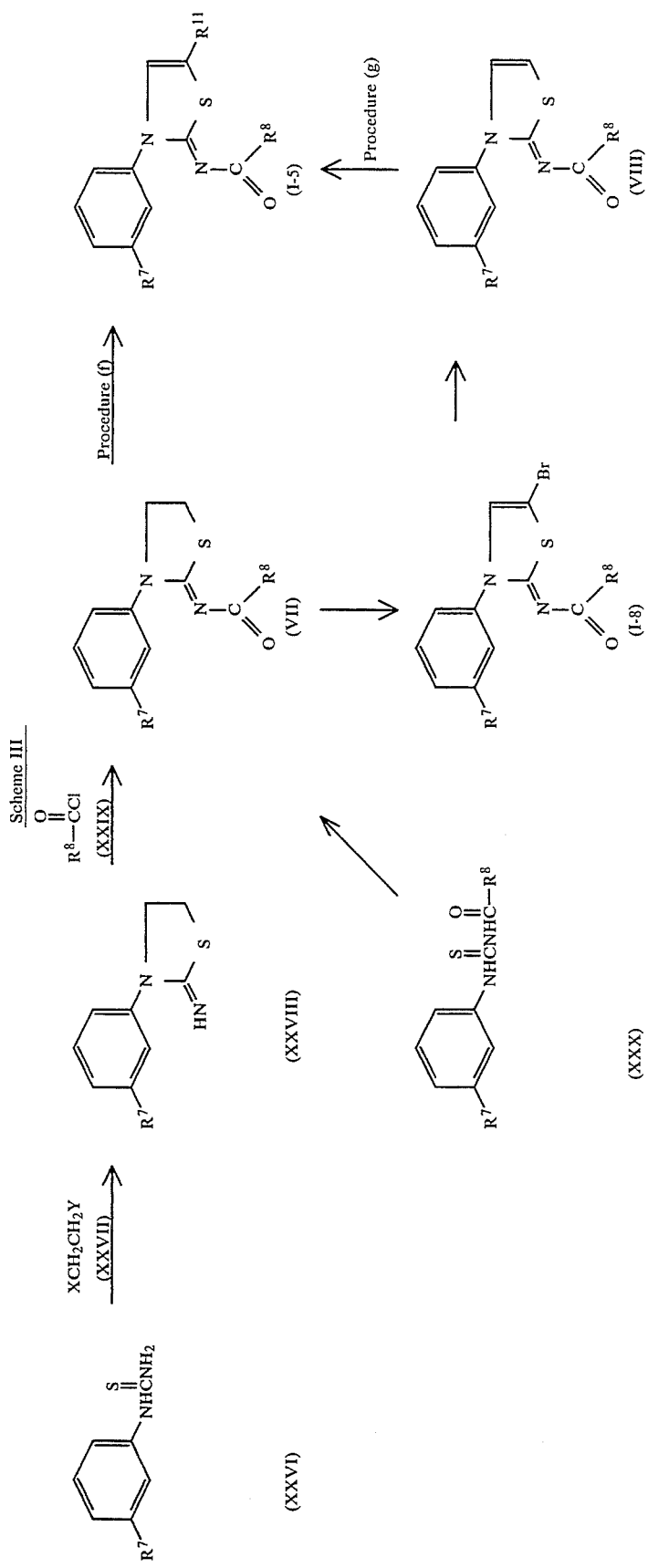

wherein $R^1$, $R^2$, $R^3$ are each as defined above $R^4$ is a hydrogen atom or a methyl group, $R^5$ is a $C_1$-$C_6$ alkyl group, a $C_1$-$C_6$ alkyloxy group, a $C_1$-$C_6$ alkyloxy group substituted with $C_1$-$C_2$ alkyloxy or phenyl, a cyclo($C_3$-$C_6$) alkyl group, a cyclo($C_3$-$C_6$) alkyl group substituted with methyl, a cyclo($C_3$-$C_6$) alkyloxy group, a phenyl group, a phenoxy group, a halogen-substituted $C_1$-$C_6$ alkyl group or a benzyl group, $R^6$ is a $C_1$-$C_3$ alkyl group, $R^7$ is a halogen atom or a halogen-substituted $C_1$-$C_2$ alkyl group, $R^8$ is a $C_1$-$C_6$ alkyl group, a $C_1$-$C_6$ alkyloxy group, a $C_1$-$C_6$ alkyloxy group substituted with $C_1$-$C_2$ alkyloxy or phenyl, a phenyl group, a phenyloxy group or a halogen-substituted $C_1$-$C_6$ alkyl group. $R^9$ is a formyl group, a $C_1$-$C_6$ alkylcarbonyl group, a $C_3$-$C_4$ alkenyloxycarbonyl group, a $C_3$-$C_4$ alkynyloxycarbonyl group, a $C_1$-$C_6$ alkyloxycarbonyl group, a $C_1$-$C_6$ alkyloxycarbonyl group substituted with $C_1$-$C_2$ alkyloxy or phenyl, a cyclo($C_3$-$C_6$) alkylcarbonyl group, a cyclo($C_3$-$C_6$) alkylcarbonyl group substituted with methyl, a cyclo ($C_3$-$C_6$) alkyloxycarbonyl group, a benzoyl group, a phenoxycarbonyl group, a halogen-substituted $C_1$-$C_6$ alkylcarbonyl group or a halogen-substituted $C_1$-$C_3$ alkylsulfonyl group, $R^{10}$ is a $C_1$-$C_6$ alkyl group, a $C_1$-$C_6$ alkyl group substituted with $C_1$-$C_2$ alkyloxy or phenyl, a $C_3$-$C_4$ alkenyl group or a $C_3$-$C_4$ alkynyl group, $R^{11}$ is a chlorine atom, a bromine atom or an iodine atom and X and Y are each a halogen atom.

Procedures for production of the iminothiazoline compounds (I) as illustratively shown in the above schemes I to III will be hereinafter explained in detail.

Procedure (a)

The iminothiazoline compound (I) wherein $R^2$ is a methyl group or an ethyl group and $R^3$ is —CO—$R^5$ is obtainable by reacting the iminothiazolidine compound (II) with a base.

The reaction is usually carried out in a solvent at a temperature of 0 to 200° C. for a period of 1 to 30 hours. In the reaction, the base is used in an amount of 1 to 50 equivalents to one equivalent of the iminothiazolidine compound (II). As the solvent, there may be exemplified aliphatic hydrocarbons (e.g. hexane, heptane), aromatic hydrocarbons (benzene, toluene, xylene), ethers (e.g. diisopropyl ether, dioxane, tetrahydrofuran, diethylene glycol dimethyl ether), alcohols (e.g. methanol, ethanol, isopropanol, t-butanol, octanol, cyclohexanol, methylcellosolve, diethylene glycol, glycerin), acid amides (e.g. N,N-dimethylformamide), sulfur compounds (e.g. dimethylsulfoxide, sulforan), water, etc. and their mixtures. Examples of the base are an inorganic base (e.g. sodium hydroxide, potassium hydroxide, sodium carbonate, potassium carbonate), an alkali metal alkoxide (e.g. sodium methoxide, sodium ethoxide, potassium t-butoxide, sodium t-butoxide), etc.

After completion of the reaction, the reaction mixture may be subjected to after-treatment in a per se conventional manner such as extraction with an organic solvent and concentration. If necessary, any purification method (e.g. chromatography, recrystallization, etc.) may be further adopted to give the objective compound (I), i.e. Compound (I-1).

Procedure (b)

The iminothiazoline compound (I) wherein $R^2$ is a methyl group or an ethyl group and $R^3$ is —CO—$R^5$ can be also produced by the reaction of the iminothiazolidine compound (III) with a base.

This reaction is usually carried out in a solvent at a temperature of 0 to 200° C. for a period of 1 to 30 hours. The base may be used in an amount of 0.5 to 50 equivalents to one equivalent of the iminothiazolidine compound (III).

The solvent and the base may be chosen from those as exemplified in Proceudre (a). Also, the reaction mixture may be subjected to after-treatment in the same way as in Procedure (a) to give the objective compound (I), i.e. Compound (I-1).

Procedure (c)

The iminothiazoline compound (I) wherein $R^2$ is a methyl group or an ethyl group and $R^3$ is the same as represented by $R^9$ is obtainable by the reaction of the iminothiazoline compound (IV) with an acid chloride (V), an acid anhydride (XIV) or an acid (XXXI) in the presence of a base.

The reaction is usually performed in a solvent at a temperature of 0 to 200° C. for a period of 1 to 30 hours. The acid chloride (V), the acid anhydride (XIV) or the acid (XXXI) may be used in an amount of 1 to 10 equivalents to one equivalent of the iminothiazoline compound (IV), and the base may be used in an amount of 1 to 50 equivalents to one equivalent of the iminothiazoline compound (IV). When the reaction is carried with the acid (XXXI) as the reagent, a condensing agent such as dicyclohexylcarbodiimide or 1-ethyl-3-(3-dimethylaminopropyl)carbodiimide is normally used in an amount of 1 to 10 equivalents to one equivalent of the iminothiazoline compound (IV). As the solvent, there may be exemplified aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethylene glycol dimethyl ether), ketones (e.g. acetone, methylethylketone, methylisobutylketone, isophorone, cyclohexanone), esters (e.g. ethyl formate, ethyl acetate, butyl acetate, diethyl carbonate), nitro compounds (e.g. nitroethane, nitrobenzene), nitriles (e.g. acetonitrile, isobutyronitrile), tertiary amines (e.g. pyridine, triethylamine, N,N-diethylaniline, tributylamine, N-methylmorpholine), acid amides (e.g. N,N-dimethylformamide), sulfur compounds (e.g. dimethylsulfoxide, sulforan), etc. and their mixtures. As the base, there may be employed an organic base (e.g. pyridine, triethylamine, N,N-diethylaniline) or the like.

After completion of the reaction, the reaction mixture may be subjected to after-treatment in the same manner as in Procedure (a) to give the objective compound (I), i.e. Compound (I-2).

Procedure (d)

The iminothiazoline compound (I) wherein $R^2$ is a methyl group or an ethyl group and $R^3$ is —CO—$OR^{10}$ can be produced by reacting the iminothiazoline compound (I-6) with the alcohol (XV) in the presence of a base.

The reaction is usually carried out in a solvent at a temperature of 0 to 200° C. for a period of 1 to 30 hours. The alcohol (XV) and the base may be used respectively in amounts of 1 to 10 equivalents and 0.5 to 50 equivalents to one equivalent of the iminothiazoline compound (I-6). As the solvent, there are employed aliphatic hydrocarbons (e.g. hexane, heptane, ligroin), aromatic hydrocarbons (e.g. benzene., toluene, xylene), ethers (e.g. diethyl ether, diisopropyl ether, dioxane, tetrahydrofuran, diethyleneglycol dimethyl ether), alcohols (e.g. methanol, ethanol, isopropanol, t-butanol, octanol, cyclohexanol, methylcellosolve, diethyleneglycol, glycerin), acid amides (e.g. N,N-dimethylformamide), sulfur compounds (e.g. dimethylsulfoxide, sulforan), water, etc. and their mixtures. Examples of the base may be an inorganic base (e.g. sodium hydroxide, potassium hydroxide), an alkali metal alkoxide (e.g. sodium methoxide, sodium ethoxide), etc.

After completion of the reaction, the reaction mixture may be subjected to after-treatment in the same manner as in Procedure (a) to give the objective compound (I), i.e. Compound (I-3).

Procedure (e)

The iminothiazoline compound (I) wherein $R^2$ is a methyl group or an ethyl group and $R^3$ is —CONH—$R^6$ is prepared by reacting the iminothiazolidine compound (VI) with a base.

This reaction is usually carried out in a solvent at a temperature of 0 to 200° C. for a period of 1 to 30 hours. The base is used in an amount of 0.5 to 50 equivalents to one equivalent of the iminothiazolidine compound (VI). Examples of the solvent are those as used in Procedure (a). As the base, there may be employed an alkali metal alkoxide (e.g. sodium methoxide, sodium ethoxide) or the like.

After completion of the reaction, the reaction mixture is subjected to after-treatment in the same way as in Procedure (a) to give the objective compound (I), i.e. Compound (I-4).

Procedure (f)

The iminothiazoline compound (I) wherein $R^1$ is the same as represented by $R^7$, $R^2$ is a chlorine atom, a bromine atom or an iodine atom and $R^3$ is —CO—$R^8$ is prepared by reacting the iminothiazoline compound (VII) with a halogenating agent.

The reaction is usually carried out in a solvent at a temperature of 50 to 150° C. for a period of 2 to 10 hours. The halogenating agent may be used in an amount of 1 to 10 equivalents to one equivalent of the compound (VII). Examples of the solvent are aliphatic hydrocarbons (e.g. hexane, heptane), halogenated hydrocarbons (e.g. chloroform, carbon tetrachloride, dichloroethane), ethers (e.g. diisopropyl ether, dioxane, tetrahydrofuran, diethyleneglycol dimethyl ether), etc. and their mixtures. As the halogenating agent, there may be exemplified N-chlorosuccinimide, N-bromosuccinimide, N-iodosuccinimide, etc.

After completion of the reaction, the reaction mixture is after-treated in the same way as in Procedure (a) to give the objective compound (I), i.e. Compound (I-5) or (I-8).

Procedure (g)

The iminothiazoline compound (I) wherein $R^1$ is the same as represented by $R^7$, $R^2$ is a chlorine atom, a bromine atom or an iodine atom and $R^3$ is —CO—$R^8$ is obtainable by reacting the iminothiazoline compound (VIII) with a halogenating agent.

The reaction is usually carried out in a solvent at a temperature of 50 to 150° C. for a period of 2 to 10 hours. The halogenating agent may be used in an amount of 1 to 10 equivalents to one equivalent of the iminothiazoline compound (VIII). Examples of the solvent and the halogenating agent may be those as exemplified in Procedure (f).

After completion of the reaction, the reaction mixture is after-treated in the same way as in Procedure (a) to give the objective compound (I), i.e. Compound (I-5).

Typical examples of the iminothiazoline compounds (I) produced by the above procedures are shown in Table 1.

TABLE 1 (I)

| $R^1$ | $R^2$ | $R^3$ |
|---|---|---|
| $CF_3$ | $CH_3$ | $CO_2C_2H_5$ |
| $CF_3$ | $C_2H_5$ | $CO_2C_2H_5$ |
| $CF_3$ | $CH_3$ | $CO_2CH_3$ |
| $CF_3$ | $CH_3$ | $CO_2(i)C_3H_7$ |
| $CF_3$ | $C_2H_5$ | $CO_2(i)C_3H_7$ |
| $CF_3$ | $CH_3$ | $CO_2(n)C_3H_7$ |
| $CF_3$ | $CH_3$ | $CO_2$-cyclopentyl |
| $CF_3$ | $CH_3$ | $CO_2$-cyclohexyl |
| $CF_3$ | $CH_3$ | $CO_2CH_2CH_2OCH_3$ |
| $CF_3$ | $CH_3$ | $CO_2CH_2CH=CH$ |
| $CF_3$ | $CH_3$ | $CO_2CH_2CH(CH_3)_2$ |
| $CF_3$ | $CH_3$ | $CO_2CH_2C\equiv CH$ |
| $CF_3$ | $CH_3$ | $CO_2CH(CH_3)C_2H_5$ |
| $CF_3$ | $C_2H_5$ | $CO_2CH_2C\equiv CH$ |
| $CF_3$ | $C_2H_5$ | $CO_2CH_3$ |
| $CF_3$ | $C_2H_5$ | $COCH_2CH(CH_3)_2$ |
| $CF_3$ | $CH_3$ | CO-cyclopropyl |
| $CF_3$ | $CH_3$ | $COCH_2C(CH_3)_3$ |
| $CF_3O$ | $CH_3$ | $CO_2C_2H_5$ |
| $CF_3O$ | $CH_3$ | $CO_2(i)C_3H_7$ |
| $CF_3$ | $C_2H_5$ | CO-cyclopropyl |
| $CF_3$ | $C_2H_5$ | $CO_2(n)C_3H_7$ |
| $CF_3$ | $CH_3$ | $CO(i)C_3H_7$ |
| $CF_3$ | $CH_3$ | $CO(n)C_4H_9$ |
| $CF_3O$ | $C_2H_5$ | $CO_2(i)C_3H_7$ |
| $CF_3$ | $CH_3$ | CO-(methylcyclopropyl) |
| $CF_3$ | $CH_3$ | $COC(CH_3)_3$ |
| $CF_3$ | $CH_3$ | $COCH_2CH(CH_3)_2$ |
| $CF_3$ | $CH_3$ | $COCH(CH_3)CH_2CH_3$ |
| $CF_3$ | $CH_3$ | $COC_6H_5$ |
| F | $CH_3$ | $CO_2C_2H_5$ |
| Br | $CH_3$ | $CO_2C_2H_5$ |
| Cl | $CH_3$ | $CO_2C_2H_5$ |
| I | $CH_3$ | $CO_2C_2H_5$ |
| $CF_3CF_2$ | $C_2H_5$ | $CO_2(i)C_3H_7$ |
| $CF_2HCF_2O$ | $C_2H_5$ | $CO_2(i)C_3H_7$ |

TABLE 1-continued (I)

structure: R¹-phenyl-N=C(N(R³))-S-C=CH-R² (iminothiazoline)

| R¹ | R² | R³ |
|---|---|---|
| CF₃ | C₂H₅ | CO₂CH₂CH₂C≡CH |
| CF₃ | C₂H₅ | CO(n)C₅H₁₁ |
| CF₃ | C₂H₅ | CO(n)C₅H₁₁ |
| CF₃ | C₂H₅ | COC₂H₅ |
| CF₃ | C₂H₅ | COCH₃ |
| CF₃ | Br | CO₂C₂H₅ |
| CF₃ | Cl | CO₂C₂H₅ |
| CF₃ | Br | COC₆H₅ |
| CF₃ | Br | CO₂(i)C₃H₇ |
| CF₃ | Br | CO₂CH₃ |
| CF₃ | Br | CO(n)C₃H₇ |
| CF₃ | Br | CO₂(n)C₄H₉ |
| F | Br | CO₂C₂H₅ |
| Br | Br | CO₂C₂H₅ |
| Cl | Br | CO₂C₂H₅ |
| CF₃ | Br | CO₂C₆H₅ |
| CF₃ | Br | CO₂(n)C₃H₇ |
| CF₃ | I | CO₂C₂H₅ |
| CF₃ | Br | CO₂CH₂C₆H₅ |
| CF₃ | CH₃ | CO₂CH₂C≡CCH₃ |
| CF₃ | C₂H₅ | CONHC₃H₇ |
| CF₃ | CH₃ | COC₂H₅ |
| CF₃ | CH₃ | CO(n)C₃H₇ |
| CF₃ | CH₃ | COCH₂C₆H₅ |
| CF₃ | C₂H₅ | CO(n)C₃H₇ |
| CF₃ | C₂H₅ | CO(i)C₃H₇ |
| CF₃ | C₂H₅ | COCH₂C(CH₃)₃ |
| F | CH₃ | CO(CH₂)₃Cl |
| Cl | CH₃ | COCH₂CH₂Br |
| CF₃ | CH₃ | CONHC₂H₅ |
| CF₃ | C₂H₅ | SO₂CF₃ |
| CF₃ | CH₃ | COCH₂CH₂Cl |
| CF₃ | Br | COCH₃ |
| CF₃ | CH₃ | CO(n)C₅H₁₁ |
| CF₃ | CH₃ | CO-cyclopentyl |
| CF₃ | CH₃ | CO₂CH₂CH=CHCH₃ |
| CF₃ | CH₃ | COCH₂Cl |
| CF₃ | CH₃ | CO(CH₂)₃Cl |
| CF₃ | CH₃ | CO-cyclohexyl |
| CF₃ | C₂H₅ | CONHCH₃ |
| CF₃ | CH₃ | COCH₂Br |
| CF₃ | CH₃ | COCF₃ |
| CF₃ | C₂H₅ | COCF₃ |
| CF₃ | Br | COCF₃ |
| CF₃ | CH₃ | COC₂F₅ |
| CF₃ | C₂H₅ | COC₂F₅ |
| CF₃ | CH₃ | COC₃F₇ |
| CF₃O | CH₃ | COCH₃ |
| CF₃O | CH₃ | COCF₃ |
| CF₃ | C₂H₅ | CO-(2-methylcyclopropyl) |
| CF₃ | CH₃ | COCHF₂ |
| CF₃ | CH₃ | COCH₂F |
| CF₃ | C₂H₅ | COCHF₂ |
| CF₃O | C₂H₅ | COCH₃ |
| CF₃O | C₂H₅ | COCF₃ |
| CF₃O | CH₃ | COCHF₂ |
| CF₃O | C₂H₅ | COCHF₂ |

The compounds (III), (XI), (IV) and (VIII) used as the starting materials for production of the iminothiazoline compound (I) in the above procedures are novel and may be produced, for instance, by the processes as set forth below.

Compound (III)

The compound (III) is produced by reacting the aniline compound (IX) with an isothiocyanate (X).

The reaction is usually carried out in a solvent at a temperature of 0 to 200° C. for a period of 1 to 30 hours. The isothiocyanate (X) is normally used in an amount of 1 to 5 equivalents to one equivalent of the aniline compound (IX). As the solvent, there may be employed aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethyleneglycol dimethyl ether), ketones (e.g. acetone, methylethylketone, methylisobutylketone, isophoron, cylcohexanone), nitro compounds (e.g. nitroethane, nitrobenzene), acid amides (e.g. N,N-dimethylformamide), sulfur compounds (e.g. dimethylsulfoxide, sulforan), etc. and their mixtures. For acceleration of the reaction, an acid (e.g. sulfuric acid) or a base (e.g. sodium methoxide) may be present in the reaction system.

After completion of the reaction, the reaction mixture is after-treated by a per se conventional procedure. For instance, the mixture is extracted with an organic solvent, followed by concentration. If necessary, the reaction product may be purified by chromatography or recrystallization to give the objective compound (III).

Still, the above reaction can proceed through the compound (III) to the iminothiazoline compound (I) in a single operation depending upon the kind of the compound (III) and the reaction conditions (cf. Procedure (b)).

In an alternative way, the compound (III) may be produced by reacting the iminothiazolidine compound (II) with a base. This reaction is ordinarily carried out in a solvent at a temperature of 0 to 200° C. for a period of 1 to 30 hours. The base is used normally in an amount of 1 to 50 equivalents to one equivalent of the iminothiazolidine compound (II). As the solvent, there may be employed aliphatic hydrocarbons (e.g. hexane, heptane, ligroin, petroleum ether), aromatic hydrocarbons (e.g. benzene, toluene, xylene), ethers (e.g. diethyl ether, diisopropyl ether, dioxane, tetrahydrofuran, diethyleneglycol dimethyl ether), alcohols (e.g. methanol, ethanol, isopropanol, t-butanol, octanol, cyclohexanol, methylcellosolve, diethylene glycol, glycerin), acid amides (e.g. formamide, N,N-dimethylformamide, acetamide), sulfur compounds (e.g. dimethylsulfoxide, sulforan), etc. and their mixtures. Examples of the base are an inorganic base (e.g. sodium hydroxide, potassium hydroxide), an alkali metal alkoxide (e.g. sodium methoxide, sodium ethoxide, sodium t-butoxide), etc.

After completion of the reaction, the reaction mixture is after-treated in the same manner as in the previous reaction.

In another alternative way, the compound (III) is obtainable by reacting the iminothiazolidine compound (XI) with an acid chloride (XII) in the presence of a base.

This reaction is usually performed in a solvent at a temperature of 0 to 200° C. for a period of 1 to 30 hours. The acid chloride (XII) and the base are respectively used in amounts of 1 to 10 equivalents and 1 to 50 equivalents to one equivalent of the iminothiazolidine compound (XI). Examples of the solvent are aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethyleneglycol dimethyl ether), ketones (e.g. acetone, methylethylketone, methylisobutylketone, isophoron, cyclohexanone), esters (e.g. ethyl formate, ethyl acetate, butyl acetate, diethyl carbonate), nitro compounds (e.g. nitroethane, nitrobenzene), nitriles (e.g. acetonitrile, isobutyronitrile), tertiary amines (e.g. pyridine, triethylamine, N,N-diethylaniline, tributylamine, N-methylmorpholine), acid amides (e.g. formamide, N,N-dimethylformamide, acetamide), sulfur compounds (e.g. dimethylsulfoxide, sulforan), etc. and their mixtures. As the base, there may be used an organic base (e.g. pyridine, triethylamine, N,N-diethylaniline) or the like.

After completion of the reaction, the reaction mixture is after-treated in the same manner as in the previous reaction.

Typical examples of the compound (III) as obtainable by the above procedures are as follows:

TABLE 2

(III)

| R¹ | R⁴ | R⁵ |
|---|---|---|
| CF₃ | H | OC₂H₅ |
| CF₃ | CH₃ | OC₂H₅ |
| CF₃ | H | OCH₃ |
| CF₃ | H | O(i)C₃H₇ |
| CF₃ | CH₃ | O(i)C₃H₇ |
| CF₃ | H | O(n)C₃H₇ |
| CF₃ | H | O-cyclopentyl |

TABLE 2-continued (III)

| R¹ | R⁴ | R⁵ |
|---|---|---|
| CF₃ | H | O-cyclohexyl |
| CF₃O | CH₃ | cyclopropyl |
| Cl | H | CH₃ |
| Br | CH₃ | C₂H₅ |
| CF₃ | CH₃ | CF₃ |
| CF₃O | H | CF₃ |
| CF₃ | H | CF₃ |
| CF₃ | H | CH₂C(CH₃)₃ |
| CF₃ | H | cyclopropyl |
| CF₃ | H | CH₂CH₂Cl |
| CF₃ | CH₃ | C₂H₅ |
| CF₃ | H | (i)C₃H₇ |
| CF₃ | CH₃ | (n)C₄H₉ |
| CF₃ | H | OC₆H₅ |
| CF₃ | CH₃ | (CH₂)₄Cl |
| CF₃CF₂ | H | C₂H₅ |
| F | H | C₂H₅ |
| CF₂HCF₂O | CH₃ | C₆H₅ |
| CF₃ | CH₃ | CHF₂ |
| CF₃ | H | CHF₂ |

Compound (XI)

The compound (XI) can be produced by reacting the aniline compound (XIII) with hydrogen sulfide.

This reaction may be accomplished in a solvent in the presence of a base at a temperature of 0 to 30° C. for a period of 5 minutes to 5 hours. Hydrogen sulfide is used in an equimolar amount or more to the aniline compound (XIII), while the base may be employed in a catalytic amount. As the solvent, there may be exemplified aliphatic hydrocarbons (e.g. hexane, heptane, ligroin, petroleum ether), ethers (e.g. diethyl ether, diisopropyl ether, dioxane, tetrahydrofuran, diethylene glycol dimethyl ether), alcohols (e.g. methanol, ethanol, isopropanol, t-butanol, octanol, cyclohexanol, methylcellosolve, diethylene glycol, glycerin), nitro compounds (e.g. nitroethane, nitrobenzene), tertiary amines (e.g. pyridine, triethylamine, N,N-diethylaniline, tributylamine, N-methylmorpholine), acid amies (e.g. formamide, N,N-dimethylformamide, acetamide), sulfur compounds (e.g. dimethylsulfoxide, sulforan), etc. and their mixtures. The base is chosen from an organic base (e.g. pyridine, triethylamine and N,N-diethylaniline) or the like.

After completion of the reaction, the reaction mixture is post-treated in the same manner as in the previous reaction.

Typical examples of the compounds (XI) as obtainable by the above procedure are shown in Table 3.

TABLE 3

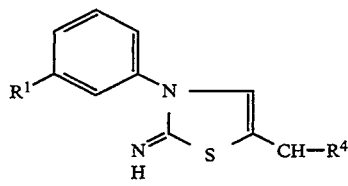
(XI)

| R¹ | R⁴ |
|---|---|
| $CF_3$ | H |
| $CF_3$ | $CH_3$ |
| $CF_3O$ | H |
| F | H |
| Cl | H |
| Br | $CH_3$ |
| $CF_3CF_2$ | $CH_3$ |
| $CF_2HCF_2O$ | $CH_3$ |

Compound (IV)

The compound (IV) is produced by reacting the iminothiazoline compound (I-7) with trifluoroacetic acid.

This reaction is usually carried out in the presence or absence of a solvent at a temperature of 0 to 100° C. for a period of 1 to 10 hours. The amount of trifluoroacetic acid to be used as the reagent is usually from about 1 to 100 equivalents to one equivalent of the iminothiazoline compound (I-7). As the solvent, there may be employed aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ketones (e.g. acetone, methylethylketone, methylisobutylketone, isophoron, cylcohexanone), nitro compounds (e.g. nitroethane, nitrobenzene), nitriles (e.g. acetonitrile, isobutyronitrile), acid amides (e.g. formamide, N,N-dimethylformamide, acetamide), sulfur compounds (e.g. dimethylsulfoxide, sulforan), water, etc. and their mixtures.

After completion of the reaction, the reaction mixture is post-treated in the same manner as in the previous reaction.

Besides, the compound (IV) is obtainable by reacting the compound (I-9) with aqueous hydrochloric acid.

This reaction is usually performed in a solvent at a temperature of 0 to 200° C. for a period of 0.5 to 30 hours. Hydrochloric acid is used in an amount of 1 to 1000 equivalents to one equivalent of the compound (I-9). Examples of the solvent are alcohols (e.g. methanol, ethanol, isopropanol, methyl cellosolve), ethers (e.g. diethyl ether, diisopropyl ether, dioxane, tetrahydrofuran), water, etc., and their mixtures.

After completion of the reaction, the reaction mixture is post-treated in the same manner as in the previous reaction.

Typical examples of the compounds (IV) as obtained by the above procedure are shown in Table 4.

TABLE 4

(IV)

| R¹ | R⁴ |
|---|---|
| $CF_3$ | H |
| $CF_3$ | $CH_3$ |
| $CF_3O$ | $CH_3$ |
| F | H |
| Cl | H |
| Br | $CH_3$ |
| $CF_3CF_2$ | $CH_3$ |
| $CF_2HCF_2O$ | $CH_3$ |

Compound (VIII)

The compound (VIII) is obtainable by reacting the iminothiazoline compound (I-8) with a reducing agent such as tributyltin hydride.

The reaction is usually performed in a solvent at a temperature of 0 to 200° C. for a period of 1 to 30 hours. The amount of the reducing agent may be from about 1 to 10 equivalents to one equivalent of the compound (I-8).

There may be used as the solvent aliphatic hydrocarbons (e.g. hexane, heptane, ligroin, petroleum ether), aromatic hydrocarbons (e.g. benzene, toluene, xylene), ethers (e.g. diethyl ether, diisopropyl ether, dioxane, tetrahydrofuran, diethyleneglycol dimethyl ether), ketones (e.g. acetone, methylethylketone, methylisobutylketone, isophoron, cyclohexanone), esters (e.g. ethyl formate, ethyl acetate, butyl acetate, diethyl carbonate), nitro compounds (e.g. nitroethane, nitrobenzene), nitriles (e.g. acetonitrile, isobutyronitrile), acid amides (e.g. N,N-dimethylformamide), sulfur compounds (e.g. dimethylsulfoxide, sulforan), etc. and their mixtures.

After completion of the reaction, the reaction mixture is post-treated in the same manner as in the previous reaction.

Typical examples of the compound (VIII) as obtainable by the above procedure are shown in Table 5.

TABLE 5

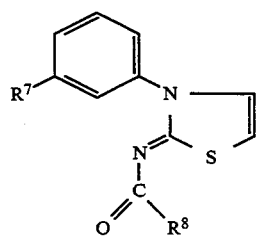
(VIII)

| R⁷ | R⁸ |
|---|---|
| $CF_3$ | $OC_2H_5$ |
| $CF_3$ | $C_2H_5$ |
| $CF_3$ | $CH_3$ |
| $CF_3CF_2$ | $CH_3$ |
| F | $OCH_3$ |
| Cl | $OCH_2CH_2CH_3$ |
| Br | $(CH_2)_3CH_3$ |

TABLE 5-continued (VIII)

[Structure: substituted phenyl-N=C(S-CH=CH-)-N-C(=O)-R⁸ with R⁷ on phenyl ring]

| R⁷ | R⁸ |
|---|---|
| CF₃CF₂ | —O—⟨phenyl⟩ |
| CF₃ | —⟨phenyl⟩ |
| CF₃ | CF₃ |
| CF₃O | CF₃ |

The iminothiazolidine compound (II) may be produced by the method as described in J. Am. Chem. Soc., p. 1079 (1984). Namely, the compound (II) is obtainable by reacting the aniline compound (XVI) with an isothiocyanate (X) to give the thiourea (XVII) and treating the latter with a halogenating agent. Alternatively, the compound (II) can be produced by reacting the thiourea (XVII: R=OEt) with sodium methoxide to give the thiourea (XIX) and reacting the latter with a halogenating agent to give the iminothiazolidine compound (XX), followed by treatment with the acid chloride (XII) in the presence of a base.

The compound (IX) is obtainable by reacting the aniline compound (XXI) with an alkynyl bromide (XXII) or an alkynyl methanesulfonate (XXXI) in the presence of a base. The compound (XIII) is produced by reacting the aniline compound (XXIII) with an alkynyl bromide (XXII) in the presence of a base. The compound (I-7) is produced by reacting the compound (I-6) with potassium t-butoxide. The compound (VI) is prepared by reacting the iminothiazolidine compound

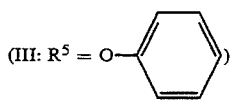
(III: R⁵ = O—⟨phenyl⟩)

with the amine (XXV).

The iminothiazolidine compound (VII) may be obtained by reacting the thiourea (XXVI) with a halide (XXVII) to give the iminothiazoline (XXVIII), followed by treatment with an acid chloride (XXIX). The iminothiazolidine compound (VII) is also produced by treating the thiourea (XXX) with a halide (XXVII).

The iminothiazoline compound (I-8) can be obtained by reacting the iminothiazolidine (VII) with a halogenating agent (cf. Procedure (f)).

For the practical usage of the iminothiazoline (I), it is usually formulated with a conventional solid or liquid carrier(s) or diluent(s) as well as a surface active agent(s) or auxiliary agent(s) into a conventional preparation form such as emulsifiable concentrate, wettable powder, suspension, granules or water dispersible granules. The content of the iminothiazoline compound (I) as the active ingredient in such preparation form is normally within a range of about 0.02 to 90% by weight, preferably of about 0.05 to 80% by weight. Examples of the solid carrier or diluent are fine powders or granules of kaolin clay, attapulgite clay, bentonite, terra alba, pyrophyllite, talc, diatomaceous earth, calcite, walnut shell powders, urea, ammonium sulfate and synthetic hydrous silica, etc. As the liquid carrier or diluent, there may be exemplified aromatic hydrocarbons (e.g. xylene, methylnaphthalene), alcohols (e.g. isopropanol, ethylene glycol, cellosolve), ketones (e.g. acetone, cyclohexanone, isophorone), vegetable oil (e.g. soybean oil, cotton seed oil), dimethylsulfoxide, N,N-dimethylformamide, acetonitrile, water, etc.

The surface active agent used for emulsification, dispersing or spreading may be of any type, for instance, either anionic or non-ionic. Examples of the surface active agent include alkylsulfates, alkylsulfonates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymer, sorbitan fatty acid esters, polyoxyethylene sorbitan fatty acid esters, etc. Examples of the auxiliary agent include ligninsulfonates, sodium alginate, polyvinyl alcohol, gum arabic, CMC (carboxymethyl cellulose), PAP (isopropyl acid phosphate), etc.

The iminothiazoline compound (I) thus formulated in any suitable preparation form is useful for pre-emergence or post-emergence control of undesired weeds by soil or foliar treatment as well as flood fallowing treatment. These treatments include application to the soil surface prior to or after planting, incorporation into the soil prior to planting or transplanting, etc. The foliar treatment may be effected by spraying the herbicidal composition containing the iminothiazoline compound (I) over the top of plants. It may also be applied directly to the weeds if care is taken to keep the chemical off the crop foliage.

The dosage of the iminothiazoline compound (I) may vary depending on the prevailing weather conditions, the formulation used, the prevailing season, the mode of application, the soil involved, the crop and weed species, etc. Generally, however, the dosage is from about 10 to 5000 grams, preferably from about 20 to 2000 grams, of the active ingredient per hectare. The herbicidal composition of the invention formulated in the form of an emulsifiable concentrate, a wettable powder or a suspension may ordinarily be employed by diluting it with water at a volume of about 100 to 1000 liters per hectare, if necessary, with addition of an auxiliary agent such as a spreading agent. The composition formulated in the form of granules may be normally applied as such without dilution.

Examples of the spreading agent include, in addition to the surface active agents as noted above, polyoxyethylene resin acid (ester), ligninsulfonate, abietylenic acid salt, dinaphthylmethanedisulfonate, paraffin, etc.

The iminothiazoline compound (I) is useful as a herbicide to be employed for paddy filed, crop field, orchards, pasture land, lawns, forests, non-agricultural fields, etc. Further, the iminothiazoline compound (I) may be also used together with any other herbicide to improve its activity as a herbicide, and in Some cases, a synergistic effect can be expected. Furthermore, it may be applied in combination with an insecticide, an acaricide, a nematocide, a fungicide, a plant growth regulator, a fertilizer, a soil improver, etc.

The present invention will be explained more in detail by way of Preparation Examples, Reference Examples, Formulation Examples and Test Examples, to which however the invention is not limited in any way.

Practical and presently preferred embodiments for production of the iminothiazoline compound (I) are illustratively shown in the following examples.

Preparation Example 1 (Procedure (a))

A solution of 2-ethoxycarbonylimino-3-(3-trifluoromethylphenyl)-5-bromomethylthiazolidine (0.7 g) and potassium t-butoxide (0.25 g) in t-butanol (30 ml) was refluxed for 5 hours. After removal of the solvent under reduced pressure, the concentrated residue was extracted with chlorofom (100 ml), washed with water and dried over anhydrous magnesium sulfate. The solvent was removed under reduced pressure,-and the residue was subjected to column chromatography to give 0.36 g of 2-ethoxycarbonylimino-3-(3-trifluoromethylphenyl)-5-methylthiazoline (Compound No. 1).

Preparation Example 2 (Procedure (b))

A solution of 2-ethoxycarbonylimino-3-(3-trifluoromethylphenyl)-5-methylenethiazolidine (2.0 g) and sodium methoxide (28 % methanolic solution; 1.2 g) in ethanol (50 ml) was refluxed for 30 minutes. After removal of the solvent under reduced pressure, the concentrated residue was extracted with chlorofom (200 ml), washed with water and dried over anhydrous magnesium sulfate. The solvent was removed under reduced pressure, and the residue was subjected to column chromatography to give 1.6 g of 2-ethoxycarbonylimino-3-(3-trifluoromethylphenyl) 5-methylthiazoline (Compound No. 1).

Preparation Example 3 (Procedure (c))

To a solution of 2-imino-3-(3-trifluoromethylphenyl)-5-ethylthiazoline (0.5 g) and triethylamine (0.6 g) in chloroform (30 ml), is ovaleryl chloride (0.8 g) was dropwise added under stirring at room temperature, and stirring was continued for 2 hours. After removal of the solvent under reduced pressure, the concentrated residue was extracted with ethyl acetate (100 ml), washed with water and dried over anhydrous magnesium sulfate. The solvent was removed under reduced pressure, and the residue was subjected to column chromatography to give 0.2 g of 2-isovalerylimino-3-(3-trifluoromethylphenyl) 5-ethylthiazoline (Compound No. 16).

Preparation Example 4 (Procedure (c))

To a mixture of 2-imino-3-(3-trifluoromethylphenyl)-5-methylthiazoline hydrochloride (7.2 g) and triethylamine (7.4 g) in ethyl acetate (100 ml), trifluoroacetic acid anhydride (5.2 g) was added under stirring at room temperature, and stirring was continued for 3 hours. The residue was washed with water and dried over anhydrous magnesium sulfate. The solvent was removed under reduced pressure to give a crystalline residue which was recrystallized from isopropanol to afford 2-trifluoroacetylimino-3-(3-trifluoromethylphenyl)-5-methylthiazoline (Compound No. 54) (7.5 g). m.p., 128.1° C.

Preparation Example 5 (Procedure (c))

A mixture of 2-imino-3-(3-trifluoromethylphenyl)-5-methylthiazoline hydrochloride (0.42 g), triethylamine (2.2 g), 1-ethyl-3-(3-dimethylaminopropyl)carbodiimide hydrochloride (0.8 g) and difluoroacetic acid (0.75 g) in chloroform (10 ml) was refluxed for 8 hours. The residue was washed with aqueous hydrochloric acid and aqueous potassium carbonate and dried over magnesium sulfate. The solvent was removed under reduced pressure, and the residue was subjected to column chromatography to give 2-difluoroacetylimino-3-(3-trifluoromethylphenyl)-5-methylthiazoline (Compound No. 63) (0.3 g). m.p., 117.9° C.

Preparation Example 6 (Procedure (d))

A solution of 2-ethoxycarbonylimino-3-(3-trifluoromethylphenyl)-5-methylthiazoline (1.0 g) and sodium methoxide (28% methanolic solution; 0.6 g) in methanol (30 ml) was refluxed for 10 hours. After removal of the solvent, the residue was extracted with chloroform (100 ml), washed with water and dried over anhydrous magnesium. The solvent was removed under reduced pressure, and the residue was subjected to column chromatography to give 0.8 g of 2-methoxycarbonylimino-3- (3-trifluoromethylphenyl) 5-methylthiazoline (Compound No. 3).

Preparation Example 7 (Procedure (e))

A solution of 2- (N-ethylcarbamoylimino) -3-(3-trifluoromethylphenyl)-5-methylenethiazolidine (0.2 g) and sodium methoxide (28% methanolic solution; 0.2 g) in methanol (30 ml) was refluxed for 10 hours. After removal of the solvent, the residue was extracted with chloroform (100 ml), washed with water and dried over anhydrous magnesium. The solvent was removed under reduced pressure, and the residue was subjected to column chromatography to give 0.1 g of 2-(N-ethylcarbamoylimino)-3-(3-trifluoromethylphenyl)-5-methylthiazoline (Compound No. 44).

Preparation Example 8 (Procedure (f))

A solution of 2-ethoxycarbonylimino-3-(3-trifluoromethylphenyl)thiazolidine (1.6 g) and N-bromosuccinimide (2 g) in chloroform (50 ml) was refluxed for 10 hours. After cooling, the reaction mixture was washed with an aqueous sodium sulfite solution and dried over anhydrous magnesium sulfate. The solvent was removed under reduced pressure, and the residue was subjected to column chromatography to give 0.9 g of 2-ethoxycarbonylimino-3-(3-trifluoromethylpheny)-5-bromothiazoline (Compound No. 30).

Preparation Example 9 (Procedure (g))

A solution of 2-ethoxycarbonylimino-3-(3-trifluoromethylphenyl)thiazoline (0.5 g) and N-iodosuccinimide (0.4 g) in chloroform (30 ml) was refluxed for 20 hours. After cooling, the reaction mixture was washed with an aqueous sodium sulfite solution and dried over anhydrous magnesium sulfate. The solvent was removed under reduced pressure, and the residue was subjected to column chromatography to give 0.1 g of 2-ethoxycarbonylimino-3-(3-tri-fluoromethylphenyl)-5-iodothiazoline (Compound No. 42).

In the same manner as above, the iminothiazoline compounds (I) as shown in Table 6 were obtained.

TABLE 6

(I)

[Structure: R¹-substituted phenyl-N=C(N(R³))-S-C(=CH₂)-R² thiazolidine ring]

| Compound No. | R¹ | R² | R³ | Melting point (°C.) |
|---|---|---|---|---|
| 1 | CF₃ | CH₃ | CO₂C₂H₅ | 115.5 |
| 2 | CF₃ | C₂H₅ | CO₂C₂H₅ | 97.1 |
| 3 | CF₃ | CH₃ | CO₂CH₃ | 136.8 |
| 4 | CF₃ | CH₃ | CO₂(i)C₃H₇ | 126.0 |
| 5 | CF₃ | C₂H₅ | CO₂(i)C₃H₇ | 91.8 |
| 6 | CF₃ | CH₃ | CO₂(n)C₃H₇ | 91.1 |
| 7 | CF₃ | CH₃ | CO₂-cyclopentyl | 134.0 |
| 8 | CF₃ | CH₃ | CO₂-cyclohexyl | 155.7 |
| 9 | CF₃ | CH₃ | CO₂CH₂CH₂OCH₃ | 103.0 |
| 10 | CF₃ | CH₃ | CO₂CH₂CH=CH₂ | 99.1 |
| 11 | CF₃ | CH₃ | CO₂CH₂CH(CH₃)₂ | 101.6 |
| 12 | CF₃ | CH₃ | CO₂CH₂C≡CH | 145.5 |
| 13 | CF₃ | CH₃ | CO₂CH(CH₃)C₂H₅ | 107.8 |
| 14 | CF₃ | C₂H₅ | CO₂CH₂C≡CH | 125.8 |
| 15 | CF₃ | C₂H₅ | CO₂CH₃ | 141.4 |
| 16 | CF₃ | C₂H₅ | COCH₂CH(CH₃)₂ | 116.3 |
| 17 | CF₃ | CH₃ | CO-cyclopropyl | 132.6 |
| 18 | CF₃ | CH₃ | COCH₂C(CH₃)₃ | 123.1 |
| 19 | CF₃O | CH₃ | CO₂C₂H₅ | 102.1 |
| 20 | CF₃O | CH₃ | CO₂(i)C₃H₇ | 120.0 |
| 21 | CF₃ | C₂H₅ | CO-cyclopropyl | 111.7 |
| 22 | CF₃ | C₂H₅ | CO₂(n)C₃H₇ | 75.7 |
| 23 | CF₃ | CH₃ | CO(i)C₃H₇ | 139.6 |
| 24 | CF₃ | CH₃ | CO(n)C₄H₉ | 122.6 |
| 25 | CF₃O | C₂H₅ | CO(i)C₃H₇ | 63.6 |
| 26 | CF₃ | CH₃ | CO-(1-methylcyclopropyl) | 100.3 |
| 27 | CF₃ | CH₃ | COC(CH₃)₃ | 94.7 |
| 28 | CF₃ | CH₃ | COCH₂CH(CH₃)₂ | 92.4 |
| 29 | CF₃ | CH₃ | COCH(CH₃)CH₂CH₃ | 58.3 |
| 30 | CF₃ | Br | CO₂C₂H₅ | 136.8 |
| 31 | CF₃ | Cl | CO₂C₂H₅ | 138.2 |
| 32 | CF₃ | Br | COC₆H₅ | 182.4 |
| 33 | CF₃ | Br | CO₂(i)C₃H₇ | 106.0 |
| 34 | CF₃ | Br | CO₂CH₃ | 106.8 |
| 35 | CF₃ | Br | CO(n)C₃H₇ | 141.4 |
| 36 | CF₃ | Br | CO₂(n)C₄H₉ | 104.9 |
| 37 | F | Br | CO₂C₂H₅ | 172.4 |
| 38 | Br | Br | CO₂C₂H₅ | 155.4 |
| 39 | Cl | Br | CO₂C₂H₅ | 147.7 |
| 40 | CF₃ | Br | CO₂C₆H₅ | 137.7 |
| 41 | CF₃ | Br | CO₂(n)C₃H₇ | 107.0 |
| 42 | CF₃ | I | CO₂C₂H₅ | 121.6 |
| 43 | CF₃ | Br | CO₂CH₂C₆H₅ | 95.2 |
| 44 | CF₃ | CH₃ | CONHC₂H₅ | 93.2 |
| 45 | CF₃ | C₂H₅ | SO₂CF₃ | 115.5 |
| 46 | CF₃ | CH₃ | COCH₂CH₂Cl | 155.2 |
| 47 | CF₃ | CH₃ | COC₂H₅ | 164.6 |
| 48 | CF₃ | CH₃ | COC₃H₇ | 111.0 |
| 49 | CF₃ | CH₃ | COCH₂C₆H₅ | 126.4 |
| 50 | CF₃ | C₂H₅ | COCH₃ | 87.8 |
| 51 | CF₃ | C₂H₅ | COC₂H₅ | 117.5 |
| 52 | CF₃ | C₂H₅ | CO(n)C₃H₇ | 119.0 |
| 53 | CF₃ | C₂H₅ | CO(i)C₃H₇ | 96.6 |
| 54 | CF₃ | CH₃ | COCF₃ | 128.1 |
| 55 | CF₃ | C₂H₅ | COCF₃ | 92.0 |
| 56 | CF₃ | Br | COCF₃ | 113.2 |
| 57 | CF₃ | CH₃ | COC₂F₅ | 98.5 |
| 58 | CF₃ | C₂H₅ | COC₂F₅ | 94.1 |
| 59 | CF₃ | CH₃ | COC₃F₇ | 61.7 |
| 60 | CF₃O | CH₃ | COCH₃ | 150.8 |
| 61 | CF₃O | CH₃ | COCF₃ | 104.7 |
| 62 | CF₃ | C₂H₅ | CO-(1-methylcyclopropyl) | 98.3 |
| 63 | CF₃ | CH₃ | COCHF₂ | 117.9 |
| 64 | CF₃ | CH₃ | COCH₂F | 135.7 |
| 65 | CF₃ | C₂H₅ | COCHF₂ | 96.3 |

Practical embodiments for preparation of various starting compounds and intermediates are shown in the following examples.

Compound (III)

Preparation Example 8

A mixture of 3-trifluoromethylaniline (30 g) and propargyl bromide (12 g) was stirred at 80° C. for 3 hours, followed by filtration of the reaction mixture. The filtrate was subjected to column chromatography to give N-propargyl-3-trifluoromethylaniline (7 g). A solution of N-propargyl-3-trifluoromethylaniline thus obtained (5.1 g) and ethoxycarbonyl isothiocyalate (3.7 g) in tetrahydrofuran (100 ml) was stirred at room temperature for 8 hours, and the solvent was removed under reduced pressure. The concentrated residue was extracted with chloroform (200 ml), washed with water and dried over anhydrous magnesium sulfate. After removal of the solvent, the residue was subjected to column chromatography to give 5.7 g of 2-ethoxycarbonlimino-3- (3-trifluoromethylphenyl)-5-methylene-thiazolidine (Compound (i)).

Preparation Example 9

A solution of 2-ethoxycarbonylimino-3-(3-trifluoromethylphenyl)-5-bromomethylthiazolidine (0.7 g) and potassium t-butoxide (0.25 g) in t-butanol (30 ml) was refluxed for 5 hours, and the solvent was distilled off under reduced pressure. The residue was extracted with chloroform (100 ml), washed with water and dried over anhydrous magnesium sulfate. After removal of the solvent, the residue was subjected to column chromatography to give 0.25 g of 2-ethoxycarbonylimino-3-(3-trifluoromethyl-phenyl)-5-methylenethiazolidine (Compound (i)).

Preparation Example 10

A solution of 2-imino-3-(3-trifluoromethylphenyl)-5-methylenethiazoline (0.5 g), triethylamine (0.3 g) a ethyl chlorocarbonate (0.5 g) in tetrahydrofuran (30 ml) was stirred at room temperature for 24 hours, followed removal of the solvent under reduced pressure. The residue was extracted with ethyl acetate (100 ml), washed with water and dried over anhydrous magnesium sulfate. After removal of the solvent, the residue was subjected to column chromatography to give 0.2 g of 2-ethoxycarbonylimino-3 (3-trifluoromethylphenyl)-5-methylenethiazoline (Compound (i)).

In the same manner as above, the compounds (III) as shown in Table 7 were obtained.

TABLE 7

(III)

| Compound No. | $R^1$ | $R^4$ | $R^5$ | Melting point (°C.) |
|---|---|---|---|---|
| i | $CF_3$ | H | $OC_2H_5$ | 97.2 |
| ii | $CF_3$ | $CH_3$ | $OC_2H_5$ | 137.2 |
| iii | $CF_3$ | $CH_3$ | $O(i)C_3H_7$ | 128.9 |
| iv | $CF_3$ | H | ◁ | 129.9 |
| v | $CF_3$ | H | $CH_2C(CH_3)_3$ | 103.2 |
| vi | $CF_3$ | H | $(i)C_3H_7$ | 97.8 |
| vii | $CF_3$ | H | $OC_6H_5$ | 133.5 |
| viii | $CF_3$ | H | $CH_2CH_2Cl$ | 74.2 |

Compound (XI)

Preparation Example 11

To a solution of N-cyano-3-trifluoromethylaniline (5.0 g) in acetone (100 ml), potassium carbonate (7.4 g) and propargyl bromide (3.5 g) were added, and the resultant mixture was stirred at room temperature for 10 hours, followed by filtration of the reaction mixture. The solvent was removed from the filtrate by distillation under reduced pressure, and the residue was subjected to column chromatography to give N-cyano-N-propargyl-3-trifluoromethylaniline (3.8 g). The thus obtained N-cyano-N-propargyl-3-trifluoromethylaniline (1 g) and a catalytic amount of triethylamine were dissolved in methanol (30 ml), and the resultant mixture was cooled to 0° C. Hydrogen sulfide was gradually introduced into the mixture for 20 minutes while keeping the temperature at 0° C., followed by introduction of nitrogen gas to remove hydrogen sulfide. The solvent was removed by distillation, and the residue was subjected to column chromatography to give 0.2 g of 2-imino-3-(3-trifluoromethylphenyl)-5-methylenethiazolidine (Compound (ix)).

In the same manner as above, the compound (XI) as shown in Table 8 was obtained.

TABLE 8

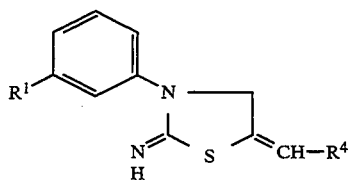

(XI)

| Compound No. | $R^1$ | $R^4$ | $^1$H-NMR (δ) |
|---|---|---|---|
| ix | $CF_3$ | H | 7.2–7.9 (4H), 6.4 (1H), 5.0–5.2 (2H), 4.7 (2H) |

Compound (IV)

Preparation Example 12

A mixture of 2-(t-butoxycarbonylimino)-3-(3-trifluoromethylphenyl)-5-ethylthiazoline (1 g) and trifluoroacetic acid (3 g) in chloroform (20 ml) was stirred at room temperature for 3 hours, followed by addition of water (50 ml) thereto. The resultant mixture was neutralized with potassium carbonate, extracted with chloroform and dried over anhydrous magnesium sulfate. The solvent was removed by distillation under reduced pressure, and the residue was subjected to column chromatography to give 0.3 g of 2-imino-3- (3-trifluoromethylphenyl) -5-ethylthiazoline (Compound (x)).

Preparation Example 13

A mixture of 2- (acetylimino)-3- (3-trifluoromethylphenyl)-5-methylthiazoline (1 g) and hydrochloric acid (38%, 4 ml) in ethanol-water (1:2, 15 ml) was refluxed for 3 hours. Ethanol was removed by distillation under reduced pressure, and the residue was neutralized with potassium carbonate, extracted with ethyl acetate and dried over anhydrous magnesium sulfate. The solvent was removed by distillation under reduced pressure to give 0.4 g of 2-imino-3- (3-trifluoromethylphenyl) -5-methylthiazoline (Compound (xi)).

In the same manner as above, the compound (IV) as shown in Table 9 was obtained.

TABLE 9

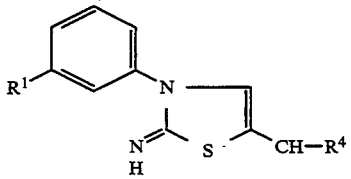

(IV)

| Compound No. | $R^1$ | $R^4$ | $^1$H-NMR (δ) |
|---|---|---|---|
| x | $CF_3$ | $CH_3$ | 7.5–7.9 (4H), 6.4 (1H), 5.3 (1H), 2.5 (q. 2H), 1.25 (t, 3H) |
| xi | $CF_3$ | H | 7.4–7.9 (5H), 6.4 (1H), 2.1 (3H) |

Compound (VIII)

Preparation Example 14

A solution of 2-ethoxycarbonylimino-3-(3-trifluoromethylphenyl)-5-bromothiazoline (4.7 g), tributyltin hydride (6.9 g) and a catalytic amount of benzoyl peroxide in tetrahydrofuran (100 ml) was refluxed for 10 hours. The solvent was removed by distillation, and the residue was washed with hexane. Recrystallization from a mixture of hexane and ethanol gave 2.85 g of 2-ethoxycarbonylimino-3-(3-trifluoromethylphenyl) thiazoline (Compound (xii)).

In the same manner as above, the compound (VIII) as shown in Table 10 was obtained.

TABLE 10

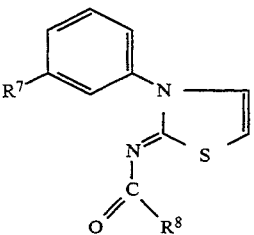
(VIII)

| Compound No. | $R^7$ | $R^8$ | Melting point (°C.) |
|---|---|---|---|
| xii | $CF_3$ | $OC_2H_5$ | 134.5 |

Compound (II)

Reference Example 1

A solution of N-allyl-3-trifluoromethylanilien (3 g) and ethoxycarbonyl isothiocyanate (2.1 g) in chloroform (50 ml) was stirred at room temperature for 3 hours, followed by removal of the solvent. The residue was subjected to column chromatography to give N-allyl-N-(3-trifluoromethylphenyl)-N'-ethoxycarbonylthiourea (3.5 g). The thus obtained thiourea (1 g) and N-bromosuccinimide (0.6 g) were dissolved in chloroform (50 ml), and the solution was stirred at room temperature for 6 hours. The solvent was removed by distillation, and the residue was extracted with ethyl ether. The extract was washed with an aqueous sodium sulfite solution and an aqueous sodium hydroxide solution in order, dried over anhydrous magnesium sulfate and concentrated under reduced pressure to give 1.2 g of 2-ethoxycarbonylimino-3-(3-trifluoromethylphenyl)-5-bromomethylthiazolidine. m.p., 108.3° C.

Reference Example 2

A solution of N-crotyl-N-(3-trifluoromethylphenyl)-N'-ethoxycarbonylthiourea (6 g) and sodium methoxide (28 % methanolic solution; 6.6 g) in methanol (100 ml) was refluxed for 2 days. After removal of the solvent, the residue was extracted with chloroform, washed with water and dried over anhydrous magnesium sulfate. The solvent was removed under reduced pressure, and the residue was subjected to column chromatography to give N-crotyl-N-(3-trifluoromethylphenyl)thiourea (2.4 g). The thus obtained thiourea (2.0 g) and N-bromosuccinimide (1.4 g) were dissolved in chloroform (50 ml), and the resultant solution was stirred at room temperature for 5 hours, washed with an aqueous sodium sulfite solution and dried over anhydrous magnesium sulfate. After removal of the solvent by distillation under reduced pressure, the residue was subjected to column chromatography to give 0.8 g of 2-imino-3-(3-trifluoromethylphenyl)-5-(1-bromoethyl)thiazolidine.

The above obtained 2-imino-3-(3-trifluoromethylphenyl)-5-(1-bromoethyl)thiazolidine (0.8 g) and triethylamine (1 g) were dissolved in tetrahydrofuran (50 ml), followed by dropwise addition of isopropyl chlorocarbonate (0.5 g). The resultant mixture was stirred at room temperature for 3 hours. The solvent was removed by distillation under reduced pressure. The residue was extracted with chloroform, washed with water and dried over anhydrous magnesium sulfate. After removal of the solvent, the residue was subjected to column chromatography to give 0.1 g of 2-isopropyloxycarbonylimino-3-(3-trifluoromethylphenyl)-5-(1-bromoethyl)thiazolidine.

Compound (VI)

Reference Example 3

To a solution of 2-phenoxycarbonylimino-3-(3-trifluoromethylphenyl)-5-methylenethiazolidine (0.5 g) in diethyl ether (30 ml), 70% ethylamine (10 ml) was added, and the resultant mixture was stirred at room temperature for 5 hours. The reaction mixture was extracted with diethyl ether. The extract was washed with water, dried over anhydrous magnesium sulfate and concentrated under reduced pressure. The residue was subjected to column chromatography to give 0.23 g of 2-(N-ethylcarbamoyl)-3-(3-trifluoromethylphenyl)-5-methylenethiazolidine. m.p., 118.5° C.

Compound (VII)

Reference Example 4

A solution of N-(3-trifluoromethylphenyl)thiourea (6.1 g), dibromoethane (5.7 g) and anhydrous potassium carbonate (11.5 g) in acetone (60 ml) was refluxed for 1 day. The solvent was removed by distillation therefrom, and the residue was extracted with ethyl ether, washed with water, dried over anhydrous magnesium sulfate and subjected to column chromatography to give 7.5 g of 2-imino-3-(3-trifluoromethylphenyl)thiazolidine. The thus obtained 2-imino-3-(3-trifluoromethylphenyl) thiazolidine (1.0 g), n-butyl chlorocarbonate (0.61 g) and triethylamine (1.2 g) were dissolved in tetrahydrofuran, and the resultant solution was stirred at room temperature for 5 hours. The solvent was removed, and the residue was extracted with ethyl acetate, washed with water and dried over anhydrous magnesium sulfate. After removal of the solvent, the residue was subjected to column chromatography to give 0.57 g of 2-butoxycarbonylimino-3-(3-trifluoromethylphenyl) thiazolidine.

Reference Example 5

A solution of N-(3-trifluoromethylphenyl)-N'-ethoxycarbonylthiourea (1.8 g), dibromoethane (1.29 g) and anhydrous potassium carbonate (2.6 g) in acetone (20 ml) was refluxed for 5 hours. The solvent was removed by distillation, and the residue was extracted with diethyl ether. The extract was washed with water, dried over anhydrous magnesium sulfate and concentrated under reduced pressure. The residue was recrystallized from a mixture of hexane and ethanol to give 1.63 g of 2-ethoxycarbonylimino-3-(3-trifluoromethylphenyl)-thiazolidine. m.p., 75.8° C.

Practical embodiments of the herbicidal composition according to the invention are illustratively shown below wherein parts are by weight. The compound number of the active ingredient corresponds to the one in Table 6.

Formulation Example 1

Fifty parts of any one of Compound Nos. 1 to 65, 3 parts of calcium ligninsulfonate, 2 parts of sodium laurylsulfate and 45 parts of synthetic hydrous silica are well mixed while being powdered to obtain wettable powder.

Formulation Example 2

Five parts of any one of Compound No. 1 to 65, 15 parts of "Toxanone P8L®" (a commercial surface active agent; Sanyo Kasei K. K.) and 80 parts of cyclohexanone are well mixed to obtain emulsifiable concentrate.

Formulation Example 3

Two parts of any one of Compound No. 1 to 65, 1 part of synthetic-hydrous silica, 2 parts of calcium ligninsulfonate, 30 parts of bentonite and 65 parts of kaolin clay are well mixed while being powdered. The mixture is then kneaded with water, granulated and dried to obtain granules.

Formulation Example 4

Twenty-five parts of any one of Compound No. 1 to 65 are mixed with 3 parts of polyoxyethylene sorbitan monooleate, 3 parts of carboxymethyl cellulose (CMC) and 69 parts of water and pulverized until the particle size of the mixture becomes less than 5 microns to obtain a suspension.

The biological data of the iminothiazoline compound (I) as the herbicide will be illustratively shown in the following Test Examples wherein the phytotoxicity to crop plants and the herbicidal activity on weeds were observed visually as to the degree of germination as well as the growth inhibition and rated with an index 0, 1, 2, 3, 4, 5, 6, 7, 8, 9 or 10, the numeral "0" indicating no material difference as seen in comparison with the untreated plants and the numeral "10" indicating the complete inhibition or death of the test plants. The compound number in the biological data corresponds to the one in Table 6.

The compounds as shown in Table 11 were used for comparison.

TABLE 11

| Compound No. | Structure | Remarks |
|---|---|---|
| (A) | Cl—C₆H₄—CH₂SC(=O)—N(C₂H₅)₂ | Benthiocarb (commercial herbicide) |
| (B) | 3-F-C₆H₄ iminothiazoline with OC₂H₅ carbamate | EP-A-0349282 |
| (C) | 3-Br-C₆H₄ iminothiazoline with OC₂H₅ carbamate | EP-A-0349282 |
| (D) | 3-EtO-C₆H₄ iminothiazoline with OC₂H₅ carbamate | EP-A-0349282 |
| (E) | 3-Cl-C₆H₄ iminothiazoline with OC₂H₅ carbamate | EP-A-0349282 |
| (F) | 3-F₃C-C₆H₄ iminothiazoline with OCH₃ carbamate | EP-A-0349282 |
| (G) | 3-F₃C-C₆H₄ iminothiazoline with OC₂H₅ carbamate | EP-A-0349282 |
| (H) | 3-F₃C-C₆H₄ iminothiazoline with OCH(CH₃)₂ carbamate | EP-A-0349282 |

TABLE 11-continued

| Compound No. | Structure | Remarks |
|---|---|---|
| (I) | F$_3$C-phenyl-N=C(S-CH(C$_2$H$_5$)CH$_2$-)N-C(=O)OC$_2$H$_5$ | EP-A-0349282 |
| (J) | F$_3$C-phenyl-N=C(S-CH(CH$_3$)CH$_2$-)N-C(=O)OC$_2$H$_5$ | EP-A-0349282 |

Test Example 1

Cylindrical plastic pots (diameter, 10 cm; height, 10 cm) were filled with upland field soil, and the seeds of japanese millet, tall morningglory and velvetleaf were sowed therein and covered with soil. A designated amount of the test compound formulated in an emulsifiable concentrate as in Formulation Example 2 was diluted with water, and the dilution was sprayed onto the soil surface by means of a small hand sprayer at a spray volume of 1,000 liters per hectare. The test plants were grown in a greenhouse for 20 days, and the herbicidal activity was examined. The results are shown in Table 12.

TABLE 12

| Compound No. | Dosage (g/ha) | Herbicidal activity Japanese millet | Tall morningglory | Velvetleaf |
|---|---|---|---|---|
| 1 | 2000 | 9 | 9 | 10 |
|  | 500 | 9 | 7 | 9 |
| 2 | 2000 | 9 | 10 | 10 |
|  | 500 | 7 | 7 | 7 |
| 3 | 2000 | 10 | 9 | 10 |
|  | 500 | 9 | 7 | 8 |
| 4 | 2000 | 10 | 10 | 10 |
|  | 500 | 10 | 10 | 10 |
|  | 125 | 10 | 10 | 8 |
| 5 | 2000 | 10 | 10 | 10 |
|  | 500 | 9 | 10 | 8 |
|  | 125 | 8 | 9 | — |
| 6 | 2000 | 10 | 10 | 10 |
|  | 500 | 10 | 10 | — |
| 7 | 2000 | 9 | 10 | 10 |
|  | 500 | 9 | 8 | — |
| 8 | 2000 | 8 | 9 | — |
|  | 500 | 7 | 8 | — |
| 9 | 2000 | 10 | 10 | 10 |
|  | 500 | 10 | 10 | — |
| 10 | 2000 | 10 | 10 | 10 |
|  | 500 | 10 | 7 | — |
| 11 | 2000 | 10 | 10 | 9 |
|  | 500 | 10 | 9 | — |
| 12 | 2000 | 10 | 10 | 10 |
|  | 500 | 10 | 7 | 8 |
| 13 | 2000 | 10 | 10 | 10 |
| 14 | 2000 | 9 | 9 | 10 |
| 15 | 2000 | 10 | 9 | 10 |
| 16 | 2000 | 10 | 10 | 9 |
|  | 500 | 10 | 10 | 9 |
| 17 | 2000 | 10 | 10 | 10 |
|  | 500 | 10 | 10 | — |
| 18 | 2000 | 10 | 10 | 10 |
|  | 500 | 9 | 9 | — |
| 19 | 2000 | 10 | 9 | 7 |
|  | 500 | 10 | 8 | — |
| 20 | 2000 | 10 | 10 | 10 |
|  | 500 | 10 | 10 | 10 |
| 21 | 2000 | 10 | 10 | — |
|  | 500 | 10 | 10 | — |
| 22 | 2000 | 10 | 10 | — |
|  | 500 | 10 | 7 | — |
| 23 | 2000 | 10 | 10 | 10 |
|  | 500 | 10 | 9 | 10 |
| 24 | 2000 | 10 | 9 | — |
|  | 500 | 10 | 9 | — |
| 25 | 2000 | 10 | 10 | 10 |
|  | 500 | 10 | 9 | 9 |
|  | 125 | 9 | 9 | 8 |
| 26 | 2000 | 10 | 10 | 10 |
|  | 500 | 10 | 10 | 10 |
|  | 125 | 9 | 9 | 8 |
| 27 | 2000 | 10 | 10 | — |
|  | 500 | 9 | 9 | — |
| 28 | 2000 | 10 | 10 | 8 |
|  | 500 | 10 | 10 | 7 |
| 29 | 2000 | 10 | 10 | 8 |
|  | 500 | 10 | 9 | 7 |
| 30 | 2000 | 9 | 10 | 10 |
|  | 500 | 9 | — | 10 |
| 31 | 2000 | 9 | 7 | 8 |
|  | 500 | 9 | — | 7 |
| 32 | 2000 | 7 | 7 | 9 |
| 33 | 2000 | 9 | 10 | 9 |
|  | 500 | 9 | 10 | 7 |
| 34 | 2000 | 10 | 10 | 10 |
|  | 500 | 9 | 8 | 10 |
| 35 | 2000 | 10 | 10 | — |
| 36 | 2000 | 9 | 10 | 7 |
|  | 500 | 7 | 8 | — |
| 40 | 2000 | — | 10 | 10 |
| 41 | 2000 | 10 | 10 | 10 |
|  | 500 | 10 | 10 | 10 |
|  | 125 | 7 | 8 | 7 |
| 42 | 2000 | 9 | 10 | 10 |
|  | 500 | 8 | 9 | 10 |
| 46 | 2000 | 10 | 10 | 9 |
|  | 500 | 10 | 7 | 7 |
| 47 | 2000 | 10 | 10 | 10 |
|  | 500 | 10 | 8 | 7 |
| 48 | 2000 | 10 | 10 | 10 |
|  | 500 | 10 | 10 | — |
| 49 | 2000 | 9 | 10 | 10 |
|  | 500 | 9 | 10 | 9 |
| 50 | 2000 | 10 | 10 | 10 |
|  | 500 | 10 | 10 | 9 |
| 51 | 2000 | 10 | 10 | 10 |
|  | 500 | 10 | 10 | 9 |
| 52 | 2000 | 10 | 10 | 10 |
|  | 500 | 10 | 10 | 9 |
| 53 | 500 | 10 | 10 | 9 |
| 54 | 500 | 10 | 10 | 10 |
|  | 125 | 10 | 10 | 10 |
| 55 | 500 | 10 | 10 | 10 |
|  | 125 | 10 | 10 | 10 |
| 56 | 500 | 9 | 9 | 9 |
|  | 125 | 8 | 8 | 8 |
| 57 | 500 | 9 | 10 | 9 |
| 58 | 500 | 10 | 10 | 8 |
|  | 125 | 9 | 7 | 7 |
| 59 | 2000 | 7 | 9 | 9 |
| 60 | 500 | 10 | 10 | 10 |
| 61 | 500 | 10 | 10 | 10 |
|  | 125 | 9 | 10 | 7 |
| 62 | 2000 | 10 | 10 | 9 |
| 63 | 500 | 10 | 10 | 10 |

TABLE 12-continued

| Compound No. | Dosage (g/ha) | Herbicidal activity | | |
|---|---|---|---|---|
| | | Japanese millet | Tall morningglory | Velvetleaf |
| | 125 | 10 | 10 | 10 |
| 64 | 500 | 10 | 10 | 10 |
| | 125 | 9 | 9 | 7 |
| 65 | 500 | 10 | 10 | 10 |
| | 125 | 9 | 10 | 10 |
| A | 2000 | 7 | 0 | 0 |
| | 500 | 0 | 0 | 0 |
| B | 2000 | 0 | 0 | 0 |
| C | 2000 | 0 | 2 | 4 |
| | 500 | 0 | 0 | 0 |
| D | 2000 | 0 | 0 | 0 |
| E | 2000 | 5 | 5 | 5 |
| | 500 | 0 | 3 | 0 |
| F | 2000 | 7 | 1 | 3 |
| | 500 | 5 | 0 | 3 |

Test Example 2

Cylindrical plastic pots (diameter, 10 cm; height, 10 cm) were filled with upland field soil, and the seeds of japanese millet, morningglory, radish and velvetleaf were sowed therein and cultivated in a greenhouse for 10 days. A designated amount of the test compound formulated in an emulsifiable concentrate as in Formulation Example 2 was diluted with water containing a spreading agent, and the dilution was sprayed over the foliage of the test plant by means of a small hand sprayer at a spray volume of 1,000 liters per hectare. The test plants were further grown in the greenhouse for 20 days, and the herbicidal activity was examined. The results are shown in Table 13.

TABLE 13

| Compound No. | Dosage (g/ha) | Herbicidal activity | | | |
|---|---|---|---|---|---|
| | | Japanese millet | Morning-glory | Radish | Velvet-leaf |
| 1 | 2000 | 9 | 9 | 10 | 9 |
| | 500 | 9 | 9 | 10 | 8 |
| 2 | 2000 | 9 | 10 | 10 | 9 |
| | 500 | 9 | 10 | 10 | 7 |
| 3 | 2000 | 9 | 10 | 10 | 10 |
| | 500 | 9 | 9 | 10 | — |
| 4 | 2000 | 10 | 10 | 10 | 10 |
| | 500 | 9 | 10 | 10 | 10 |
| | 125 | 8 | 10 | 10 | 7 |
| 5 | 2000 | 9 | 10 | 10 | 10 |
| | 500 | 9 | 10 | 10 | 10 |
| | 125 | 9 | 10 | 9 | 7 |
| 6 | 2000 | 9 | 10 | 10 | 10 |
| | 500 | 9 | 10 | 10 | 8 |
| | 125 | 9 | 10 | 10 | 7 |
| 7 | 2000 | 8 | 10 | 10 | 9 |
| | 500 | 8 | 10 | 8 | 9 |
| 8 | 2000 | — | 10 | 8 | 10 |
| 9 | 2000 | 9 | 10 | 10 | 8 |
| | 500 | 8 | 10 | 10 | — |
| 10 | 2000 | 9 | 10 | 10 | 9 |
| | 500 | 9 | 10 | 10 | — |
| 11 | 2000 | 9 | 10 | 10 | 10 |
| | 500 | 9 | 10 | 10 | 8 |
| 12 | 2000 | 9 | 10 | 10 | 10 |
| | 500 | 9 | 10 | 10 | 10 |
| | 125 | 7 | 10 | 10 | 7 |
| 13 | 2000 | 9 | 10 | 10 | 10 |
| | 500 | 9 | 10 | 10 | 9 |
| | 125 | 7 | 9 | 10 | 7 |
| 14 | 2000 | 8 | 10 | 10 | 10 |
| 15 | 2000 | 7 | 7 | 10 | 8 |
| 16 | 2000 | 9 | 10 | 10 | 9 |
| | 500 | 9 | 10 | 10 | 8 |
| 17 | 2000 | 9 | 10 | 10 | 9 |
| | 500 | 9 | 10 | 10 | 9 |
| | 125 | 8 | 10 | 9 | 8 |
| 18 | 2000 | 9 | 10 | 10 | 10 |
| | 500 | 9 | 10 | 10 | 10 |
| | 125 | 7 | 9 | 10 | 10 |
| 19 | 2000 | 9 | 10 | 7 | 7 |
| 20 | 2000 | 10 | 10 | 10 | 9 |
| | 500 | 9 | 9 | 9 | 8 |
| 21 | 2000 | 9 | 10 | 10 | 10 |
| | 500 | 9 | 10 | 9 | 10 |
| | 125 | 9 | 9 | 8 | 10 |
| 22 | 2000 | 9 | 10 | 10 | 8 |
| | 500 | 9 | 10 | 10 | 7 |
| 23 | 2000 | 10 | 10 | 10 | 10 |
| | 500 | 9 | 10 | 10 | 10 |
| | 125 | 9 | 9 | 10 | 9 |
| 24 | 2000 | 10 | 10 | 10 | 9 |
| | 500 | 9 | 10 | 10 | 8 |
| | 125 | 9 | 9 | 10 | 8 |
| 25 | 2000 | 10 | 10 | 10 | 10 |
| | 500 | 9 | 10 | 10 | 9 |
| | 125 | 9 | 10 | 9 | 9 |
| 26 | 2000 | 9 | 10 | 10 | 10 |
| | 500 | 9 | 10 | 10 | 10 |
| | 125 | 9 | 10 | 10 | 10 |
| 27 | 2000 | 10 | 10 | 10 | 10 |
| | 500 | 9 | 10 | 10 | 9 |
| | 125 | 7 | 10 | 10 | 9 |
| 28 | 2000 | 10 | 10 | 10 | 9 |
| | 500 | 9 | 10 | 9 | 9 |
| | 125 | 9 | 10 | 9 | 8 |
| 29 | 2000 | 9 | 10 | 10 | 9 |
| | 500 | 9 | 10 | 9 | 9 |
| | 125 | 8 | 10 | 9 | 7 |
| 30 | 2000 | 9 | 9 | 10 | 9 |
| | 500 | 9 | 9 | 10 | 9 |
| | 125 | 9 | 9 | 10 | 8 |
| 31 | 2000 | 10 | 10 | 10 | 10 |
| | 500 | 10 | 10 | 10 | 10 |
| | 125 | 9 | 10 | 10 | 10 |
| 32 | 2000 | — | 9 | — | 8 |
| 33 | 2000 | 9 | 10 | 10 | 10 |
| | 500 | 9 | 10 | 10 | 10 |
| | 125 | 9 | 10 | 10 | 9 |
| 34 | 2000 | 9 | 10 | 10 | 10 |
| | 500 | 9 | 9 | 10 | 10 |
| | 125 | 9 | 9 | 10 | 10 |
| 35 | 2000 | 9 | 10 | 10 | 9 |
| | 500 | 9 | 10 | 10 | 8 |
| | 125 | 8 | 10 | 10 | 8 |
| 36 | 2000 | 9 | 10 | 10 | 10 |
| | 500 | 9 | 10 | 10 | 10 |
| | 125 | 7 | 10 | 10 | 10 |
| 38 | 2000 | — | 8 | 10 | 9 |
| 39 | 2000 | — | 9 | 7 | — |
| 41 | 2000 | 10 | 10 | 10 | 10 |
| | 500 | 9 | 10 | 10 | 10 |
| | 125 | 9 | 10 | 10 | 10 |
| 42 | 2000 | 10 | 10 | 10 | 10 |
| | 500 | — | 10 | 10 | 10 |
| 43 | 2000 | — | 10 | 10 | 10 |
| | 500 | — | 10 | 10 | 10 |
| 44 | 2000 | — | 9 | 7 | — |
| 45 | 2000 | — | 10 | 10 | 8 |
| 46 | 2000 | 9 | 9 | 9 | 9 |
| | 500 | 9 | 9 | 9 | 9 |
| 47 | 2000 | 9 | 10 | 10 | 9 |
| | 500 | 9 | 10 | 10 | 9 |
| 48 | 2000 | 9 | 10 | 10 | 9 |
| | 500 | 9 | 10 | 10 | 9 |
| | 125 | 9 | 10 | 10 | 7 |
| 49 | 2000 | 9 | 10 | 10 | 9 |
| | 500 | 8 | 10 | 10 | 9 |
| | 125 | 7 | 10 | 10 | 9 |
| 50 | 2000 | 10 | 10 | 10 | 9 |
| | 500 | 10 | 10 | 10 | 9 |
| 51 | 2000 | 10 | 10 | 10 | 10 |
| | 500 | 10 | 10 | 10 | 9 |
| 52 | 2000 | 10 | 10 | 10 | 10 |
| | 500 | 10 | 10 | 10 | 9 |

TABLE 13-continued

| Compound No. | Dosage (g/ha) | Herbicidal activity | | | |
|---|---|---|---|---|---|
| | | Japanese millet | Morning-glory | Radish | Velvet-leaf |
| 53 | 500 | 10 | 10 | 10 | 9 |
| 54 | 500 | 9 | 10 | 10 | 9 |
| | 125 | 9 | 10 | 10 | 9 |
| 55 | 500 | 10 | 10 | 10 | 10 |
| | 125 | 10 | 10 | 10 | 10 |
| 56 | 500 | 9 | 10 | 10 | 9 |
| | 125 | 7 | 10 | 9 | 9 |
| 57 | 500 | 9 | 10 | 10 | 9 |
| | 125 | 9 | 10 | 10 | 9 |
| 58 | 500 | 9 | 10 | 10 | 9 |
| | 125 | 8 | 10 | 10 | 9 |
| 59 | 2000 | 8 | 10 | 10 | 9 |
| 60 | 500 | 9 | 9 | 9 | 7 |
| 61 | 500 | 9 | 9 | 9 | 10 |
| | 125 | 9 | 9 | 9 | 10 |
| 62 | 500 | 9 | 10 | 10 | 10 |
| | 125 | 9 | 10 | 10 | 9 |
| 63 | 500 | 9 | 10 | 10 | 10 |
| | 125 | 9 | 10 | 10 | 10 |
| 64 | 500 | 9 | 10 | 10 | 10 |
| | 125 | 7 | 10 | 9 | 7 |
| 65 | 500 | 10 | 9 | 10 | 10 |
| | 125 | 10 | 9 | 10 | 10 |
| A | 2000 | 9 | 2 | 1 | 0 |
| | 500 | 3 | 1 | 0 | 0 |
| B | 2000 | 1 | 3 | 0 | 0 |
| | 500 | 0 | 1 | 0 | 0 |
| C | 2000 | 3 | 6 | 3 | 4 |
| | 500 | 0 | 6 | 0 | 1 |
| D | 2000 | 0 | 2 | 1 | 0 |
| | 500 | 0 | 1 | 0 | 0 |
| E | 2000 | 3 | 6 | 2 | 1 |
| | 500 | 0 | 3 | 1 | 0 |
| F | 2000 | 6 | 2 | 5 | 4 |
| | 500 | 1 | 0 | 2 | 0 |

Test Example 3

Cylindrical plastic pots (diameter, 8 cm; height, 12 cm) were filled with paddy field soil, and the seeds of barnyardgrass (*Echinochloa oryzicola*) and hardstem bulrush (*Scirpus juncoides*) were sowed in 1 to 2 cm depth. Water was poured therein to make a flooded condition, and rice seedlings of 2-leaf stage were transplanted therein, and the test plants were grown in a greenhouse. Six days (at that time seeds began to germinate) thereafter, a designated amount of the test compound formulated in an emulsifiable concentrate as in Formulation Example 2 and diluted with water (2.5 ml) was applied to the pots by perfusion. The test plants were grown for an additional 19 days in the greenhouse, and the herbicidal activity and phytotoxicity were examined. The results are shown in Table 14.

TABLE 14

| Compound No. | Dosage (g/ha) | Herbicidal activity | | |
|---|---|---|---|---|
| | | Phytotoxicity Rice plant | Barnyard-grass | Hardstem bulrush |
| 1 | 63 | 1 | 8 | 7 |
| 2 | 250 | 1 | 10 | 9 |
| | 63 | 1 | 10 | — |
| 4 | 63 | 1 | 9 | 8 |
| 5 | 63 | 1 | 10 | 8 |
| | 16 | 1 | 10 | 8 |
| 6 | 63 | 1 | 8 | — |
| 7 | 63 | 1 | 10 | 8 |
| | 16 | 1 | 9 | — |
| 8 | 63 | 1 | 9 | — |
| 9 | 63 | 1 | 9 | 9 |
| 10 | 63 | 1 | 10 | 7 |
| 11 | 63 | 1 | 8 | — |
| 12 | 16 | 1 | 10 | 8 |

TABLE 14-continued

| Compound No. | Dosage (g/ha) | Herbicidal activity | | |
|---|---|---|---|---|
| | | Phytotoxicity Rice plant | Barnyard-grass | Hardstem bulrush |
| 13 | 63 | 1 | 9 | 7 |
| 14 | 63 | 1 | 7 | 8 |
| 15 | 250 | 1 | 10 | 9 |
| | 63 | 0 | 7 | — |
| 16 | 63 | 1 | 10 | 7 |
| 17 | 63 | 1 | 10 | 9 |
| 18 | 63 | 1 | 9 | — |
| 19 | 250 | 1 | 10 | 10 |
| | 63 | 0 | 9 | 8 |
| 20 | 63 | 1 | 10 | — |
| 21 | 63 | 1 | 10 | — |
| | 16 | 1 | 10 | 7 |
| 22 | 63 | 1 | 10 | 8 |
| | 16 | 1 | 10 | 7 |
| 23 | 63 | 1 | 10 | 9 |
| 24 | 63 | 1 | 9 | 9 |
| | 16 | 0 | 8 | 9 |
| 25 | 63 | 1 | 9 | 9 |
| 26 | 63 | 1 | 10 | 9 |
| | 16 | 1 | 9 | 9 |
| 27 | 63 | 1 | 10 | — |
| 28 | 63 | 1 | 8 | 8 |
| 30 | 250 | 0 | 10 | 10 |
| | 63 | 0 | 9 | 8 |
| 31 | 250 | 0 | 9 | 9 |
| | 63 | 0 | 9 | 8 |
| 33 | 63 | 1 | 9 | 7 |
| 34 | 63 | 1 | 9 | 8 |
| 35 | 250 | 1 | 9 | 9 |
| 36 | 250 | 1 | 10 | 9 |
| 41 | 250 | 1 | 10 | 9 |
| 42 | 63 | 1 | 9 | 8 |
| 43 | 250 | 1 | 9 | — |
| 46 | 63 | 1 | 9 | 9 |
| | 16 | 0 | 9 | 7 |
| 48 | 63 | 1 | 10 | 10 |
| | 16 | 1 | 9 | 9 |
| 49 | 63 | 1 | 9 | 8 |
| | 16 | 0 | 8 | 7 |
| 51 | 63 | 1 | 10 | 8 |
| 54 | 16 | 0 | 10 | 7 |
| 55 | 16 | 1 | 10 | — |
| 57 | 63 | 1 | 10 | 7 |
| 58 | 63 | 1 | 10 | 7 |
| 62 | 63 | 1 | 8 | — |
| 63 | 16 | 0 | 9 | 8 |
| 64 | 250 | 1 | 10 | 9 |
| 65 | 16 | 1 | 8 | 8 |
| A | 250 | 0 | 7 | 3 |
| | 63 | 0 | 2 | 0 |
| | 16 | 0 | 0 | 0 |
| B | 250 | 0 | 0 | 0 |
| C | 250 | 0 | 0 | 0 |
| D | 250 | 0 | 0 | 0 |
| E | 250 | 0 | 0 | 0 |
| F | 250 | 0 | 1 | 1 |

Test Example 4

Vats (33 cm×23 cm×11 cm) were filled with upland field soil, and the seeds of catchweed bedstraw, common chickweed, persian speedwell, field pansy and wheat were sowed therein in 1 to 2 cm depth. A designated amount of the test compound formulated in a wettable powder as in Formulation Example 1 was diluted with water, and the dilution was sprayed onto the soil surface by means of a small hand sprayer at a spray volume of 1,000 liters per hectare. The test plants were grown in a greenhouse for 20 days, and the herbicidal activity and phytotoxicity were examined. The results are shown in Table 15.

TABLE 15

| Compound No. | Dosage (g/ha) | Phytotoxicity Wheat | Herbicidal activity Catchweed bedstraw | Common chickweed | Persian speedwell | Field pansy |
|---|---|---|---|---|---|---|
| 1 | 500 | 0 | 9 | 10 | 10 | 10 |
| 2 | 500 | 0 | 8 | 10 | 10 | — |
| 4 | 500 | 1 | 9 | 10 | 10 | 10 |
| 30 | 2000 | 0 | 9 | 10 | 10 | 10 |
| 31 | 2000 | 1 | 9 | 10 | 10 | 10 |
| 33 | 2000 | 0 | 9 | 10 | 10 | 10 |
|  | 500 | 0 | 7 | 10 | 10 | 10 |
| 34 | 500 | 0 | 9 | 10 | 10 | 10 |
| 35 | 500 | 0 | 7 | 10 | 10 | 10 |
| 36 | 500 | 1 | 7 | 10 | 10 | 10 |
| 46 | 125 | 0 | 9 | 8 | 10 | 8 |
| 52 | 500 | 1 | 7 | 10 | 10 | 8 |
| A | 2000 | 0 | 0 | 0 | 10 | 10 |
| G | 2000 | 0 | 0 | 3 | 10 | 2 |
|  | 500 | 0 | 0 | 0 | 8 | 0 |

Test Example 5

Vats (33 cm×23 cm×11 cm) were filled with upland field soil, and the seeds of common chickweed, persian speedwell, blackgrass, annual bluegrass, wheat and barley were sowed therein in 1 to 2 cm depth. A designated amount of the test compound formulation in an emulsifiable concentrate as in Formulation Example 2 was diluted with water, and the dilution was sprayed onto the soil surface by means of an automatic sprayer at a spray volume of 1,000 liters per hectare. The test plants were grown in a greenhouse for 25 days, and the herbicidal activity and phytotoxicity were examined. The results are shown in Table 16.

TABLE 16

| Compound No. | Dosage (g/ha) | Phytotoxicity Wheat | Barley | Herbicidal activity Common chickweed | Persian speedwell | Blackgrass | Annual bluegrass |
|---|---|---|---|---|---|---|---|
| 3 | 125 | 0 | 1 | 10 | 10 | 8 | 9 |
| 4 | 500 | 1 | 1 | 10 | 10 | 10 | 10 |
|  | 125 | 0 | 0 | 10 | 10 | 9 | 10 |
| 5 | 125 | 0 | 1 | 10 | 10 | 9 | 10 |
| 6 | 125 | 0 | 1 | 10 | 10 | 9 | — |
| 7 | 500 | 0 | 1 | 10 | 10 | 10 | 10 |
|  | 125 | 0 | 0 | 10 | 8 | 7 | 9 |
| 9 | 125 | — | 1 | 10 | 10 | 7 | 10 |
| 10 | 125 | — | 0 | 10 | 10 | 10 | 10 |
| 12 | 125 | 0 | 1 | 9 | 7 | 7 | 8 |
| 14 | 500 | 1 | 1 | 10 | 10 | 7 | 10 |
| 17 | 500 | 0 | 1 | 10 | 10 | 10 | 10 |
|  | 125 | 0 | 0 | 9 | 10 | 8 | 10 |
| 20 | 500 | — | 0 | 10 | 10 | 10 | 10 |
|  | 125 | 1 | 0 | — | 10 | 7 | 8 |
| 21 | 500 | 0 | — | 10 | 10 | 10 | 10 |
|  | 125 | 0 | 0 | 10 | 10 | 9 | 10 |
| 22 | 500 | 0 | 1 | 7 | 10 | — | 10 |
|  | 125 | 0 | 0 | 7 | 10 | — | 8 |
| 23 | 125 | 0 | 0 | 10 | 10 | 9 | 10 |
| 24 | 125 | 0 | 1 | — | 10 | 9 | 10 |
| 26 | 500 | 0 | — | 9 | 10 | 9 | 10 |
|  | 125 | 0 | 0 | — | 10 | 8 | 10 |
| 28 | 125 | 0 | 0 | 7 | 10 | 8 | 10 |
| 30 | 500 | 0 | — | 10 | 10 | 10 | 10 |
|  | 125 | 0 | 0 | 10 | 10 | — | 8 |
| 33 | 500 | 1 | — | 10 | 10 | 9 | 9 |
|  | 125 | 0 | 1 | 10 | 10 | 8 | 9 |
| 35 | 125 | 0 | — | 9 | 10 | 10 | 9 |
| 41 | 500 | 0 | — | 10 | 10 | 10 | 10 |
|  | 125 | 0 | 1 | 9 | 10 | 10 | 10 |
| G | 125 | 0 | 0 | 0 | 6 | 0 | 0 |
| H | 500 | 0 | 0 | 1 | 5 | 2 | 0 |
|  | 125 | 0 | 0 | 0 | 5 | 0 | 0 |
| I | 125 | 0 | 0 | 0 | 6 | 2 | 4 |
| J | 125 | 0 | 0 | 0 | 6 | 0 | 0 |

Test Example 6

Vats (33 cm×23 cm×11 cm) were filled with upland field soil, and the seeds of soybean, cotton, corn, rice plant, velvetleaf and green foxtail were sowed 1 to 2 cm depth. A designated amount of the test compound formulated in a wettable powder as in Formulation Example 1 was diluted with water, and the dilution was sprayed onto the soil surface by means of a small hand sprayer at a spray volume of 1000 liters per hectare. The test plants were grown in a greenhouse for 20 days, and the herbicidal activity and phytotoxicity were examined. The results are shown in Table 17.

TABLE 17

| Compound No. | Dosage (g/ha) | Phytotoxicity Soybean | Cotton | Corn | Rice plant | Herbicidal activity Velvetleaf | Green foxtail |
|---|---|---|---|---|---|---|---|
| 30 | 500 | 1 | 0 | 0 | 0 | 9 | 10 |
| A | 500 | 1 | 0 | 1 | 1 | 0 | 6 |
| G | 500 | 0 | 0 | 0 | 0 | 0 | 0 |

Test Example 7

Vats (33 cm×23 cm×11 cm) were filled with upland field soil, and the seeds of cotton, black nightshade, johnsongrass, green foxtail were sowed therein 1 to 2 cm depth. A designated amount of the test compound formulated in an emulsifiable concentrate as in Formulation Example 2 was diluted with water, and the dilution was sprayed onto the soil surface by means of a small hand sprayer at a spray volume of 1,000 liters per hectare. The test plants were grown in a greenhouse for 20 days, and the herbicidal activity and phytotoxicity were examined. The results are shown in Table 18.

TABLE 18

| Compound No. | Dosage (g/ha) | Phytotoxicity Cotton | Herbicidal activity Black nightshade | Barnyardgrass | Green foxtail |
|---|---|---|---|---|---|
| 1 | 500 | 0 | 10 | 9 | 10 |
| 2 | 500 | 0 | 10 | — | 10 |
| 3 | 500 | 0 | 10 | 8 | 10 |
| 4 | 500 | 0 | 10 | 10 | 10 |
| 5 | 500 | 1 | 10 | 10 | 10 |
| 6 | 500 | 0 | 10 | 10 | 10 |
| 7 | 500 | 1 | 10 | 10 | 9 |
| 8 | 500 | 0 | — | 7 | 9 |
| 9 | 500 | 0 | 10 | 10 | 9 |
| 10 | 500 | 0 | 10 | 10 | 10 |
| 11 | 500 | 0 | 10 | 10 | 10 |
| 12 | 500 | 1 | 10 | 7 | 10 |
| 13 | 500 | 0 | 10 | 10 | 10 |
| 14 | 500 | 0 | 10 | 8 | 10 |
| 17 | 500 | 1 | 9 | 10 | 10 |
| 18 | 500 | 0 | 9 | 9 | 9 |
| 19 | 500 | 1 | 8 | 7 | 9 |
| 20 | 500 | 0 | 9 | 10 | 9 |
| 21 | 500 | 0 | 8 | 10 | 9 |
| 23 | 500 | 0 | 9 | 10 | 9 |
| 25 | 500 | 1 | 7 | 10 | 10 |
| 26 | 500 | 1 | 7 | 10 | 9 |
| 29 | 500 | 0 | 10 | 10 | 9 |
| 30 | 500 | 0 | 9 | 10 | 10 |
| 31 | 500 | 1 | 10 | 9 | 10 |

TABLE 18-continued

| Compound No. | Dosage (g/ha) | Phytotoxicity Cotton | Herbicidal activity Black nightshade | Barnyardgrass | Green foxtail |
|---|---|---|---|---|---|
| 33 | 500 | 1 | — | 10 | 10 |
| 34 | 500 | 0 | 10 | 9 | 10 |
| 46 | 500 | 0 | 10 | 9 | 10 |
| 48 | 500 | 1 | 10 | 10 | 9 |
| 49 | 500 | 1 | 10 | 8 | 10 |
| 50 | 500 | 0 | 10 | 10 | 8 |
| 51 | 500 | 0 | 9 | 10 | 10 |
| 52 | 500 | 0 | 9 | 10 | 10 |
| 53 | 500 | 0 | 9 | 10 | 10 |
|  | 125 | 0 | 8 | 10 | 10 |
| 54 | 500 | 1 | 10 | 10 | 10 |
|  | 125 | 0 | 9 | 10 | 10 |
| 55 | 125 | 0 | 10 | 9 | 10 |
| 57 | 500 | 1 | 10 | 10 | 10 |
| 58 | 125 | 0 | 10 | 7 | 9 |
| 62 | 500 | 0 | 10 | 8 | 9 |
| 63 | 500 | 1 | 10 | 10 | 10 |
|  | 125 | 0 | 10 | 9 | 10 |
| 64 | 500 | 0 | 10 | 10 | 10 |
|  | 125 | 0 | 10 | 8 | 10 |
| A | 500 | 0 | 0 | 6 | 6 |
| G | 500 | 0 | 0 | 0 | 0 |
| H | 500 | 0 | 1 | 1 | 1 |
| I | 500 | 1 | 0 | 2 | — |
| J | 500 | 0 | 0 | 1 | 4 |

Test Example 8

Vats (33 cm × 23 cm × 11 cm) were filled with upland field soil, and the seeds of soybean, corn, rice plant and barnyardgrass were sowed therein 1 to 2 cm depth. A designated amount of the test compound formulated in an emulsifiable concentrate as in Formulation Example 2 was diluted with water, and the dilution was sprayed onto the soil surface by means of a small hand sprayer at a spray volume of 1,000 liters per hectare. The test plants were grown in a greenhouse for 20-days, and the herbicidal activity and phytotoxicity were examined. The results are shown in Table 19.

TABLE 19

| Compound No. | Dosage (g/ha) | Phytotoxicity Soybean | Corn | Rice plant | Herbicidal activity Barnyardgrass |
|---|---|---|---|---|---|
| 1 | 500 | 1 | — | 1 | 9 |
| 3 | 500 | — | — | 1 | 8 |
| 4 | 125 | 0 | 0 | 1 | 10 |
| 5 | 125 | 0 | 1 | 0 | 9 |
| 6 | 125 | 1 | — | 1 | 9 |
| 7 | 500 | — | 1 | 1 | 10 |
| 8 | 500 | 0 | 0 | 0 | 7 |
| 9 | 500 | 1 | 0 | 1 | 10 |
| 10 | 125 | 0 | 0 | 0 | 8 |
| 11 | 125 | 0 | 1 | 1 | 9 |
| 13 | 500 | 0 | 1 | 0 | 10 |
| 17 | 125 | 0 | 1 | 1 | 9 |
| 18 | 125 | 0 | 0 | 1 | 7 |
| 19 | 500 | 0 | 0 | 1 | 7 |
| 20 | 125 | 0 | 1 | — | 10 |
| 21 | 125 | 0 | 1 | — | 9 |
| 30 | 500 | 1 | 0 | 0 | 10 |
| 31 | 500 | 0 | — | 1 | 9 |
| 33 | 125 | 0 | 1 | 1 | 9 |
| 34 | 500 | 1 | 1 | 1 | 9 |
| 35 | 250 | 1 | 1 | 1 | 9 |
| 36 | 500 | 1 | 1 | 1 | 9 |
| 41 | 125 | 1 | 0 | 1 | 9 |
| 46 | 125 | — | 1 | 1 | 9 |
| A | 500 | 1 | 1 | 1 | 6 |
| G | 500 | 0 | 0 | 0 | 0 |
| H | 500 | 0 | 0 | 0 | 1 |
| I | 500 | 0 | 1 | 0 | 2 |

TABLE 19-continued

| Compound No. | Dosage (g/ha) | Phytotoxicity Soybean | Corn | Rice plant | Herbicidal activity Barnyardgrass |
|---|---|---|---|---|---|
| J | 500 | 0 | 1 | 0 | 1 |

Test Example 9

Vats (33 cm × 23 cm × 11 cm) were filled with upland field soil, .and the seeds of cotton, morningglory and johnsongrass were sowed therein 1 to 2 cm depth. A designated amount of the test compound formulated in an emulsifiable concentrate as in Formulation Example 2 was diluted with water, and the dilution was sprayed onto the soil surface by means of a small hand sprayer at a spray volume of 1,000 liters per hectare. The test plants were grown in a greenhouse for 20 days, and the herbicidal activity and phytotoxicity were examined. The results are shown in Table 20.

TABLE 20

| Compound No. | Dosage (g/ha) | Phytotoxicity Cotton | Herbicidal activity Morningglory | Johnsongrass |
|---|---|---|---|---|
| 3 | 500 | 0 | — | 8 |
| 4 | 500 | 0 | 10 | 9 |
| 5 | 500 | 1 | 10 | 9 |
| 6 | 500 | 0 | 9 | 10 |
| 7 | 500 | 1 | 10 | 7 |
| 9 | 500 | 0 | 10 | 7 |
| 10 | 500 | 0 | 7 | 9 |
| 11 | 500 | 0 | 9 | 10 |
| 12 | 500 | 1 | — | 7 |
| 13 | 500 | 0 | — | 8 |
| 14 | 500 | 0 | 7 | — |
| 17 | 500 | 1 | 7 | 10 |
| 18 | 500 | 0 | — | 10 |
| 20 | 500 | 0 | 10 | 10 |
| 21 | 500 | 0 | 7 | 9 |
| 23 | 500 | 0 | — | 9 |
| 25 | 500 | 1 | 10 | 7 |
| 26 | 500 | 1 | 10 | 9 |
| 29 | 500 | 0 | 7 | 9 |
| 33 | 500 | 1 | 8 | 9 |
| 46 | 500 | 0 | 7 | 7 |
| 48 | 500 | 1 | 10 | 10 |
| 49 | 500 | 1 | 8 | 10 |
| 52 | 500 | 0 | 8 | 10 |
| 53 | 500 | 0 | 10 | 10 |
|  | 125 | 0 | 10 | 8 |
| 54 | 500 | 1 | 10 | 10 |
|  | 125 | 0 | 10 | 9 |
| 55 | 500 | 1 | 10 | 10 |
|  | 125 | 0 | 7 | 8 |
| 62 | 500 | 0 | 7 | 8 |
| 63 | 500 | 1 | 10 | 10 |
|  | 125 | 0 | 10 | 10 |
| 64 | 500 | 0 | 10 | 10 |
| A | 500 | 0 | 0 | 0 |
| G | 500 | 0 | 0 | 0 |
| H | 500 | 0 | 1 | 1 |
| I | 500 | 1 | 3 | 3 |
| J | 500 | 0 | 0 | 0 |

Test Example 10

Wagner's pots (1/5000 are) were filled with paddy field soil, and the seeds of barnyardgrass (*Echinochloa oryzicola*), broad-leaved weeds (i.e. common falsepimpernel, indian toothcup, waterwort) and hardstem bulrush were sowed in 1 to 2 cm depth. Water was poured therein to make a flooded condition, and rice seedling of 3-leaf stage were transplanted therein, and the test plants were grown in a greenhouse. Five days (at that time barnyardgrass began to germinate) thereafter, a designated amount of the test compound formulated in an emulsifiable concentrate as in Formulation Example 2 and diluted with water (10 ml) was applied to the pots by perfusion. The test plants were grown for an additional 19 days in the greenhouse, and the herbicidal activity and phytotoxicity were examined. The results are shown in Table 21. At the time of the treatment, the depth of water in the pots was kept at 4 cm and following two days, water was let leak a volume corresponding to a 3 cm depth per day.

TABLE 21

| Compound No. | Dosage (g/ha) | Phytotoxicity Rice plant | Herbicidal activity | | |
|---|---|---|---|---|---|
| | | | Barnyard-grass | Broad-leaved weed | Hardstem bulrush |
| 1 | 250 | 0 | 10 | 10 | 10 |
|   | 63  | 0 | 9  | 10 | 9  |
| 2 | 250 | 0 | 10 | 10 | 10 |
|   | 63  | 0 | 8  | 10 | 8  |
|   | 16  | 0 | 8  | 8  | —  |
| 3 | 250 | 1 | 10 | 10 | 10 |
|   | 63  | 0 | 9  | 10 | —  |
| 4 | 16  | 1 | 10 | 10 | 9  |
| 5 | 63  | 1 | 10 | 10 | 10 |
|   | 16  | 0 | 10 | 9  | 7  |
| 6 | 16  | 1 | 10 | 10 | —  |
| 7 | 63  | 1 | 10 | 10 | 10 |
|   | 16  | 0 | —  | 8  | 10 |
| 8 | 250 | 1 | 10 | 10 | 10 |
|   | 63  | 0 | 8  | 10 | 7  |
| 9 | 63  | 0 | 7  | 10 | 8  |
| 10| 63  | 1 | 10 | 10 | 7  |
| 17| 16  | 0 | 9  | 8  | 9  |
| 19| 63  | 0 | 8  | 9  | 8  |
| 20| 16  | 0 | 7  | 8  | —  |
| 21| 63  | 1 | 9  | 10 | 10 |
|   | 16  | 1 | 10 | 10 | 7  |
| 22| 63  | 1 | 10 | 10 | 10 |
|   | 16  | 0 | 10 | 10 | 7  |
| 30| 250 | 1 | 10 | 10 | 10 |
|   | 63  | 0 | 10 | 10 | 8  |
| 31| 250 | 0 | 10 | 10 | 10 |
| 33| 63  | 1 | 10 | 10 | 8  |
| 36| 63  | 1 | 10 | 10 | —  |
| 42| 250 | 0 | 8  | 10 | 10 |
| 46| 63  | 1 | 10 | 10 | 8  |
| 53| 16  | 0 | 10 | 10 | 7  |
| 62| 63  | 1 | 10 | 9  | 9  |
| A | 250 | 0 | 7  | 0  | 6  |
|   | 63  | 0 | 0  | 0  | 0  |
| G | 250 | 0 | 0  | 0  | 0  |
| H | 250 | 0 | 0  | 0  | 0  |

Test Example 11

Wagner's pots (1/5000 are) were filled with paddy field soil, and the seeds of barnyardgrass (*Echinochloa oryzicola*) and broad-leaved weeds (i.e. common falsepimpernel, indian toothcup, waterwort,.Ammannia multiflora) were sowed in 1 to 2 cm depth. Water was poured therein to make a flooded condition, and rice seedling of 2-leaf stage were transplanted therein, and the test plants were grown in a greenhouse. Eleven days (at that time barnyardgrass grows to the 2-leaf stage) thereafter, a designated amount of the test compound formulated in an emulsifiable concentrate as in Formulation Example 2 and diluted with water (10 ml) was applied to the pots by perfusion. The test plants were grown for an additional 20 days in the greenhouse, and the herbicidal activity and phytotoxicity were examined. The results are shown in Table 22. At the time of the treatment, the depth of water in the pots was kept at 4 cm and following two days, water was let leak a volume corresponding to a 3 cm depth per day.

TABLE 22

| Compound No. | Dosage (g/ha) | Phytotoxicity Rice plant | Herbicidal activity | |
|---|---|---|---|---|
| | | | Barnyard-grass | Broad-leaved weed |
| 2 | 250 | 0 | 8 | 8 |
| 4 | 63  | 1 | 10 | 9 |
| 5 | 250 | 1 | 10 | 8 |
|   | 63  | 0 | 9  | 8 |
| 6 | 63  | 1 | 9  | 10 |
| 17| 63  | 0 | 10 | 10 |
| 18| 250 | 1 | 10 | 8 |
| 20| 63  | 1 | 9  | 8 |
| 21| 250 | 1 | 10 | 10 |
|   | 63  | 1 | 9  | 10 |
| 22| 250 | 1 | 10 | 10 |
|   | 63  | 0 | 9  | 10 |
| 33| 63  | 0 | 10 | 7 |
| 55| 63  | 1 | 8  | 9 |
| G | 250 | 0 | 0  | 0 |
| H | 250 | 0 | 2  | 0 |
| I | 250 | 1 | 1  | 0 |

Test Example 12

Vats (33 cm×23 cm×11 cm) were filled with upland field soil, and the seeds of rice plant, morningglory, common cocklebur, velvetleaf, black nightshade, barnyardgrass and green foxtail were sowed therein and cultivated for 18 days in a greenhouse. A designated amount of the test compound formulated in an emulsifiable concentrate as in Formulation Example 2 was diluted with water, and the dilution was sprayed-over the foliage of the test plants by means of a small hand sprater at a spray volume of 500 liters per hecare. The test plants were further grown in the greenhouse for 18 days, and the herbicidal activity and phytotoxicity were examined. At the time of the application, the test plants were generally at the 1 to 4 leaf stage and in 2 to 12 cm height, although the growing stage of the test plants varied depending on their species. The results are shown in Table 23.

TABLE 23

| Compound No. | Dosage (g/ha) | Phytotoxicity Rice plant | Herbicidal activity | | | | | |
|---|---|---|---|---|---|---|---|---|
| | | | Morning-glory | Common cocklebur | Velvet-leaf | Black nightshade | Barnyard-grass | Green foxtail |
| 30 | 2000 | 0 | 9 | 9 | 9 | 9 | 9 | 9 |
| H  | 2000 | 3 | 0 | 0 | 1 | 5 | 4 | 5 |

Test Example 13

Vats (33 cm×23 cm×11 cm) were filled with upland field soil, and the seeds of cotton, giant foxtail, large crabgrass, fall panicum, shattercane, green foxtail, bermudagrass, slender amaranth, prickly sida, black nightshade, morningglory and field bindweed were sowed in 1 to 2 cm depth. A designated amount of the test compound formulated in an emulsifiable concentrate as in Formulation Example 2 was diluted with water, and the dilution was sprayed onto the soil surface by means of a small hand sprayer at a spray volume of 230 liters per hectare. The test plants were grown outdoor for 21 days, and the herbicidal activity and phytotoxicity were examined. The results are shown in Table 24.

TABLE 24

| Compound No. | Dosage (g/ha) | Phytotoxicity Cotton | Herbicidal activity | | | | | | | | | | |
|---|---|---|---|---|---|---|---|---|---|---|---|---|---|
| | | | Giant foxtail | Large crabgrass | Fall panicum | Shattercane | Green foxtail | Bermudagrass | Slender amaranth | Prickly sida | Black nightshade | Morningglory | Field bindweed |
| 4 | 400 | 0 | 10 | 10 | 10 | 10 | 10 | 10 | 10 | 9 | 10 | 10 | 8 |
| 54 | 200 | 0 | 10 | 10 | 10 | 10 | 10 | 10 | 10 | 10 | 10 | 10 | 10 |
| F | 400 | 0 | 0 | 0 | 0 | 0 | 0 | 0 | 0 | 0 | 0 | 0 | 0 |

Test Example 14

Vats (33 cm×23 cm×11 cm) were filled with upland field soil, and the seeds of wheat, persian speedwell and field pansy were sowed therein and cultivated for 31 days in a greenhouse. A designated amount of the test compound formulated in an emulsifiable concentrate as in Formulation Example 2 was diluted with water, and the dilution was sprayed over the foliage of the test plants by means of an automatic sprayer at a spray volume of 1,000 liters per hectare. The test plants were further grown in the greenhouse for 25 days, and the herbicidal activity and phytotoxicity were examined. At the time of the application, the test plants were generally at the 1 to 4 leaf stage and in 3 to 25 cm height, although the growing stage of the test plants varied depending on their species. The results are shown in Table 25.

TABLE 25

| Compound No. | Dosage (g/ha) | Phytotoxicity Wheat | Herbicidal activity | |
|---|---|---|---|---|
| | | | Persian speedwell | Field pansy |
| 54 | 500 | 1 | 10 | 10 |
| | 125 | 1 | 10 | 10 |
| J | 500 | 1 | 4 | 5 |
| | 125 | 0 | 2 | 4 |

Test Example 15

Containers (40 cm×35 cm bed) were filled with upland field soil, and the seeds of soybean, yellow foxtail, johnsongrass, southern crabgrass, giant foxtail, velvetleaf, slender amaranth, black nightshade and jimsonweed were sowed in 1 to 3 cm depth. A designated amount of the test compound formulated in an emulsifiable concentrate as in Formulation Example 2 was diluted with water, and the dilution was sprayed onto the soil surface by means of a small hand sprayer at a spray volume of 430 liters per hectare. The test plants Were grown outdoor for 52 days, and the herbicidal activity and phytotoxicity were examined. The results are shown in Table 26.

TABLE 26

| Compound No. | Dosage (g/ha) | Phytotoxicity Soybean | Herbicidal activity | | | | | | | |
|---|---|---|---|---|---|---|---|---|---|---|
| | | | Yellow foxtail | Johnsongrass | Southern crabgrass | Giant foxtail | Velvetleaf | Slender amaranth | Black nightshade | Jimsonweed |
| 54 | 100 | 0 | 10 | 10 | 10 | 10 | 10 | 10 | 10 | 9 |
| F | 100 | 0 | 0 | 0 | 0 | 0 | 0 | 0 | 0 | 0 |

What is claimed is:

1. An iminothiazolidine compound of the formula:

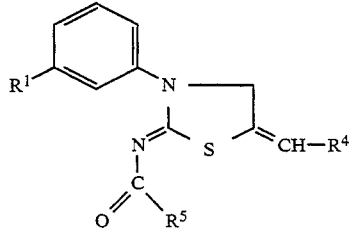

(III)

wherein $R^1$ is a halogen atom, a halogen-substituted $C_1$-$C_2$ alkyl group or a halogen-substituted $C_1$-$C_2$ alkyloxy group, $R^4$ is a hydrogen atom or a methyl group and $R^5$ is a $C_1$-$C_6$ alkyl group, a $C_1$-$C_6$ alkyloxy group, a $C_1$-$C_6$ alkyloxy group substituted with $C_1$-$C_2$ alkyloxy or phenyl, a cyclo($C_3$-$C_6$)-alkyl group, a cyclo($C_3$-$C_6$) alkyl group substituted with methyl, a cyclo($C_3$-$C_6$) alkyloxy group, a phenyl group, a phenoxy group, a halogen-substituted $C_1$-$C_6$ alkyl group or a benzyl group.

2. The compound of claim 1, wherein $R^1$ is selected from the group consisting of trifluoromethyl, trifluoromethoxy, chloro, bromo, fluoro, pentafluoroethyl and 1,2-tetrafluoroethoxy; $R^4$ is selected from the group consisting of hydrogen and methyl; and $R^5$ is selected from the group consisting of ethoxy, methoxy, isopropoxy, n-propoxy, cyclopentyloxy, cyclohexyloxy, cyclopropyl, methyl, ethyl, trifluoromethyl, tert-butylmethyl, chloroethyl, isopropyl, n-butyl, phenoxy, $(CH_2)_4Cl$, phenyl and difluoromethyl.

3. The compound of claim 1, wherein the substituents $R^1$, $R^4$ and $R^5$ are selected from the group of combinations listed in the following table:

| $R^1$ | $R^4$ | $R^5$ |
|---|---|---|
| $CF_3$ | H | $OC_2H_5$ |
| $CF_3$ | $CH_3$ | $OC_2H_5$ |
| $CF_3$ | H | $OCH_3$ |
| $CF_3$ | H | $O(i)C_3H_7$ |
| $CF_3$ | $CH_3$ | $O(i)C_3H_7$ |
| $CF_3$ | H | $O(n)C_3H_7$ |
| $CF_3$ | H | 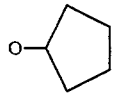 |

-continued

| R¹ | R⁴ | R⁵ |
|---|---|---|
| CF₃ | H | 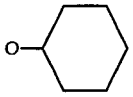 |
| CF₃O | CH₃ |  |
| Cl | H | CH₃ |
| Br | CH₃ | C₂H₅ |
| CF₃ | CH₃ | CF₃ |
| CF₃O | H | CF₃ |
| CF₃ | H | CF₃ |
| CF₃ | H | CH₂C(CH₃)₃ |
| CF₃ | H |  |
| CF₃ | H | CH₂CH₂Cl |
| CF₃ | CH₃ | C₂H₅ |
| CF₃ | H | (i)C₃H₇ |
| CF₃ | CH₃ | (n)C₄H₉ |
| CF₃ | H | OC₆H₅ |
| CF₃ | CH₃ | (CH₂)₄Cl |
| CF₃CF₂ | H | C₂H₅ |
| F | H | C₂H₅ |
| CF₂HCF₂O | CH₃ | C₆H₅ |
| CF₃ and | CH₃ | CHF₂ |
| CF₃ | H | CHF₂ |

4. An iminothiazolidine compound of the formula:

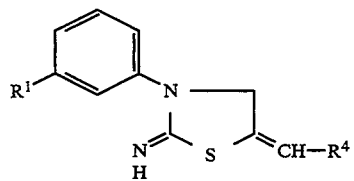

(XI)

wherein R¹ is a halogen atom, a halogen-substituted C₁–C₂ alkyl group or a halogen-substituted C₁–C₂ alkyloxy group and R⁴ is a hydrogen atom or a methyl group.

5. The compound of claim 4, wherein R¹ is selected from the group consisting of trifluoromethyl, trifluoromethoxy, fluoro, chloro, bromo, pentafluoroethyl and 1,2-tetrafluoroethoxy; and R⁴ is selected from the group consisting of hydrogen and methyl.

6. The compound of claim 4, wherein R¹ and R⁴ are selected from the group of combinations listed in the following table:

| R¹ | R⁴ |
|---|---|
| CF₃ | H |
| CF₃ | CH₃ |
| CF₃O | H |
| F | H |
| Cl | H |
| Br | CH₃ |
| CF₃CF₂ | CH₃ |
| CF₂HCF₂O | CH₃. |

7. An iminothiazoline compound of the formula:

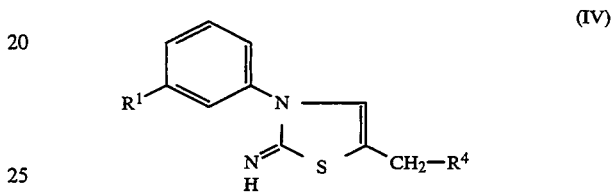

(IV)

wherein R¹ is a halogen atom, a halogen-substituted C₁–C₂ alkyl group or a halogen-substituted C₁–C₂ alkyloxy group and R⁴ is a hydrogen atom or a methyl group.

8. The compound of claim 7, wherein R¹ is selected from the group consisting of trifluoromethyl, trifluoromethoxy, fluoro, chloro, bromo, pentafluoroethyl and 1,2-tetrafluoroethoxy; and R⁴ is selected from the group consisting of hydrogen and methyl.

9. The compound of claim 7, wherein R¹ and R⁴ are selected from the group of combinations listed in the following table:

| R¹ | R⁴ |
|---|---|
| CF₃ | H |
| CF₃ | CH₃ |
| CF₃O | CH₃ |
| F | H |
| Cl | H |
| Br | CH₃ |
| CF₃CF₂ | CH₃ |
| CF₂HCF₂O | CH₃. |

* * * * *

UNITED STATES PATENT AND TRADEMARK OFFICE
CERTIFICATE OF CORRECTION

PATENT NO. : 5,426,188
DATED : June 20, 1995
INVENTOR(S) : Shinichi KAWAMURA, Keiichi IZUMI, Junichi SATO, Yuzuru SANEMITSU, Tatsuhiro HAMADA, Hideyuki SHIBATA AND Ryo SATO It is certified that error appears in the above-indentified patent and that said Letters Patent is hereby corrected as shown below:

On title page:

Changing in the "[75] Inventors:" section the incorrectly spelled city "Dyrham" to correctly read --Durham--.

Signed and Sealed this

Fifth Day of December, 1995

Attest:

BRUCE LEHMAN

Attesting Officer    Commissioner of Patents and Trademarks